(12) United States Patent
Wakil et al.

(10) Patent No.: US 7,303,281 B2
(45) Date of Patent: Dec. 4, 2007

(54) METHOD AND DEVICE FOR DETERMINING REFRACTIVE COMPONENTS AND VISUAL FUNCTION OF THE EYE FOR VISION CORRECTION

(75) Inventors: Youssef S. Wakil, Houston, TX (US); Vasyl Molebny, Kiev (UA); Ioannis G. Pallikaris, Heraklion Crete (GR); Sergiy Molebny, Houston, TX (US); Tom Padrick, Seattle, WA (US)

(73) Assignee: Tracey Technologies, LLC, Houston, TX (US)

( * ) Notice: Subject to any disclaimer, the term of this patent is extended or adjusted under 35 U.S.C. 154(b) by 496 days.

(21) Appl. No.: 10/714,454

(22) Filed: Nov. 14, 2003

(65) Prior Publication Data

US 2005/0007551 A1   Jan. 13, 2005

Related U.S. Application Data

(63) Continuation-in-part of application No. 10/137,720, filed on May 1, 2002, now Pat. No. 6,932,475, which is a continuation-in-part of application No. 09/634,487, filed on Aug. 8, 2000, now Pat. No. 6,409,345, which is a continuation-in-part of application No. PCT/US99/23327, filed on Oct. 7, 1999, application No. 10/714,454, which is a continuation-in-part of application No. PCT/US03/31610, filed on Oct. 6, 2003, and a continuation-in-part of application No. PCT/US02/41853, filed on Dec. 31, 2002, and a continuation-in-part of application No. PCT/US02/24075, filed on Jul. 29, 2002, and a continuation-in-part of application No. PCT/US02/12141, filed on Apr. 16, 2002.

(60) Provisional application No. 60/308,301, filed on Jul. 27, 2001, provisional application No. 60/284,364, filed on Apr. 16, 2001.

(30) Foreign Application Priority Data

Oct. 7, 1998 (UA) .................. 98105286
Jan. 2, 2002 (UA) ................ 2002010001
Oct. 4, 2002 (UA) ................ 2002107925

(51) Int. Cl.
*A61B 3/10* (2006.01)
(52) U.S. Cl. .............. 351/246; 351/205; 351/212; 351/221
(58) Field of Classification Search ........... 351/205, 351/212, 221, 246
See application file for complete search history.

(56) References Cited

U.S. PATENT DOCUMENTS

| | | | |
|---|---|---|---|
| 3,290,927 A | 12/1966 | Gambs | 73/80 |
| 4,190,332 A | 2/1980 | Body et al. | 351/211 |
| 4,465,348 A | 8/1984 | Lang et al. | 351/211 |
| 4,609,287 A | 9/1986 | Kohayakawa | |
| 4,691,716 A | 9/1987 | Tanne | 128/774 |
| 4,778,268 A | 10/1988 | Randle | 351/203 |
| 4,796,989 A | 1/1989 | Fukuma et al. | 351/212 |
| 5,148,205 A | 9/1992 | Guilino et al. | 351/159 |
| 5,258,791 A | 11/1993 | Penney et al. | 351/211 |
| 5,293,871 A | 3/1994 | Reinstein et al. | 128/660.06 |
| 5,414,478 A | 5/1995 | van Gelderen | 351/212 |
| 5,418,714 A | 5/1995 | Sarver | 364/413.13 |
| 5,581,405 A | 12/1996 | Meyers et al. | 359/571 |
| 5,589,897 A | 12/1996 | Sinclair et al. | 351/223 |
| 5,722,427 A | 3/1998 | Wakil et al. | 128/898 |
| 5,841,511 A | 11/1998 | D'Souza et al. | 351/212 |
| 5,847,804 A | 12/1998 | Sarver et al. | 351/206 |
| 5,875,019 A | 2/1999 | Villani | 351/211 |
| 5,953,100 A | 9/1999 | Sarver et al. | 351/206 |
| 6,000,800 A | 12/1999 | Webb et al. | 351/211 |
| 6,004,313 A | 12/1999 | Shimmick et al. | 606/5 |
| 6,082,856 A | 7/2000 | Dunn et al. | 351/160 |
| 6,199,986 B1 | 3/2001 | Williams et al. | 351/221 |
| 6,234,631 B1 | 5/2001 | Sarver et al. | 351/212 |
| 6,305,802 B1 | 10/2001 | Roffman et al. | |
| 6,382,795 B1 | 5/2002 | Lai | 351/212 |
| 6,382,797 B1 | 5/2002 | Bille et al. | 351/212 |
| 6,409,345 B1 | 6/2002 | Molebny et al. | 351/212 |
| 2003/0011745 A1 | 1/2003 | Molebny et al. | |
| 2003/0142271 A1 | 7/2003 | Ross et al. | |

2003/0199858 A1 10/2003 Schelonka

FOREIGN PATENT DOCUMENTS

| CA | 2273528 | 12/1999 |
|---|---|---|
| JP | 63242219 | 10/1988 |
| UA | 98105286 | 7/1998 |
| WO | PCT/US99/23327 | 7/1999 |

OTHER PUBLICATIONS

Corneal Topography The State of the Art by James P. Gills, Donald R. Sanders, Spencer P. Thornton, Robert G. Martin, Johnny L. Gayton, Jack T. Holladay—Chapter 5—The EyeSys 2000 Corneal Analysis System by Spencer P. Thornton, M.D. Facs and Joseph Wakil, M.D. Mee.

EyeSys 2000 Corneal Analysis System: The Ultimate in Corneal Topography from the Proven Leader (Brochure). Copyright EyeSys Technologies, Inc., 1995.

EyeSys Vista: Hand-Held Corneal Topographer (Brochure).

Ophthalmic Terminology: Speller and Vocabulary Builder—Third Edition—by Stein, Slatt, and Stein.

Contact Lenses: Update 1—Chapter 4—Corneal Topgraphy by J. James Rowsey and David J. Schanzlin (Copyright 1986 by Little, Brouwn and Company).

Contact Lenses—Chapter 17—Measurement of Corneal Curvature: Keratometer (Ophthalmometer) by Oliver H. Dabezies, Jr. and Jack T. Holladay (Copyright 1984 by Little, Brown and Company.

A Comprehensive Guide to Fitting Contact Lenses with EyeSys Pro-Fit Contact Lens Fitting Software by Beth A. Soper, C.O.A. (EyeSys System 2000—Version 3.1).

M.S. Smirnov. Measurement and wave aberration of the eye. Biofizika (Biophysics USSR), 6, pp. 687 through 703 (previously pp. 776-794, 1961). English translation of: p. 690 translation of the last paragraph continuing onto p. 691, and on p. 691 $1^{st}$, $2^{nd}$ and $3^{rd}$ full paragraphs.

Van de Brink. Measurement of the geometrical aberrations of the eye. Vision Res. 2, pp. 233-244, 1962.

N.M. Sergienko. Oftalmologicheskaya optika (Ophtalmic Optics). Moscow, Meditsina, 1991, 142 pages. English translation of: p. 30-32 text of the last paragraph referring to Figure 19 continuing onto pp. 31 and 32, and first full paragraph of p. 32.

R.H. Webb, C.M. Penney, and K.D. Thompson. Measurement of ocular local wavefront distortion with a spatially resolved refractometer. Applied Optics. 31, pp. 3678-3686, 1992.

S.G. El Hage and Berni F. Contribution of the crystalline lens to the spherical aberration of the eye. J. Opt. Soc. Am. 63, pp. 205-211, 1973.

J. Liang, B. Grimm, S. Goelz, and J. F. Bille, Objective measurement of wave aberrations of the human eye with the use of a Hartmann-Shack wave-front sensor. J Opt. Soc. A. A 11,pp. 1949-1957, 1994.

J. Liang and D.R. Williams. Aberrations and retinal image quality of the normal human eye. J Opt. Soc. Am. A 14, pp. 2873-2883, 1997.

J. Liang, D.R. Williams and D.T. Miller. Supernormal vision and high resolution retinal imaging through adaptive optics, J. Opt. Soc. Am., A 14, pp. 2884-2892, 1997.

T. Seiler, P.J. McDonnell, "Excimer laser photorefractive keratectomy", Surv. of Ophthalm., 40, pp. 89-118, 1995.

Eye Sys Technologies brochure. EyeSys Software The power that drives high performance corneal topography. EyeSys Technologies Inc., 1995.

W.D. West, OD. Corneal Topography: It's not just for surgeons anymore. Eyecare Technology, Jul./Aug. 1995.

He et al., Measurement of the wave-front aberraton of the eye by a fast psychophysical procedure, Opt. Soc. America USA, vol. 15, No. 9, Sep. 1998, pp. 2449-2456, *paragraphs [2.A.1]-[2.A.4], [0005]; figure 1*.

Navarro R et al., Monochromatic aberrations and point-spread functions of the human eye across the visual field; Journal of the Optical Society of America A, Optics and Image Science; vol. 15, No. 9 Sep. 1998, pp. 2522-2529 *p. 2523-2524; figure 1*.

*Primary Examiner*—Scott J. Sugarman
(74) *Attorney, Agent, or Firm*—Benjamin Aaron Adler

(57) ABSTRACT

A method and an instrument is provided for measuring aberration refraction of an eye with a first device for measuring the total aberration refraction of the eye and a second device for measuring the aberration refraction of the cornea of the eye. The component of aberration refraction caused by the lens caused by the lens is calculated using the measured total eye aberration refraction and the measured component of aberration refraction of the cornea mapped over the optical surfaces of the eye. Each component portion of the aberration refraction provides information usable for making appropriate corrective actions at the cornea, at the lens, or both as indicated by the mapped measurements and calculations.

46 Claims, 14 Drawing Sheets

METHOD AND DEVICE FOR DETERMINING REFRACTIVE COMPONENTS AND VISUAL FUNCTION OF THE EYE FOR VISION CORRECTION

CROSS-REFERENCE TO RELATED PATENTS AND APPLICATIONS

This is a continuation-in-part of U.S. application Ser. No. 10/137,720 filed May 1, 2002, now U.S. Pat. No. 6,932,475 which was a continuation-in-part of Ser. No. 09/634,487 filed Aug. 8, 2000 (issued as U.S. Pat. No. 6,409,345) which was a continuation-in-part of PCT Application No. PCT/US99/23327 filed Oct. 7, 1999, in which the U.S. is a designated country, and claiming priority from Ukrainian Application No. 98105286 filed Oct. 7, 1998, all relied upon for priority and all incorporated by reference herein for all legitimate purposes.

This application is also continuation-in-part of each of the following: PCT/US02/12141 filed Apr. 16, 2002, designating the U.S. and claiming priority from U.S. 60/284,364 filed Apr. 16, 2001, co-pending with the present application and co-owned at the time of the invention; PCT/US02/24075 filed Jul. 29, 2002, claiming priority from U.S. 60/308,301 filed Jul. 27, 2001, co-pending with the present application and co-owned at the time of the invention; PCT/US02/41853 filed Dec. 31, 2002, claiming priority from UA 2002010001 filed Jan. 2, 2002, co-pending with the present application and co-owned at the time of the invention; and Patent application PCT/US03/31610 filed Oct. 6, 2003 claiming priority from UA 2002107925 filed Oct. 4, 2002, co-pending with the present application and co-owned at the time of the invention; all relied upon for priority and all incorporated by reference herein for all legitimate purposes.

TECHNICAL FIELD OF THE INVENTION

The present invention relates to an ophthalmologic method and medical ophthalmologic equipment, more specifically, it relates to a method and instrument for measuring the aberration refraction of the components and visual function of the eye as a function of spatial pupil coordinates and for use of the information for correcting vision.

BACKGROUND OF THE INVENTION

For the purpose of measuring the surface shape of a cornea, a method is known of projecting a regular structure or regular patterns, such as a pattern of concentric disks onto the cornea, analyzing the reflected light and reconstructing from the analyzed data the shape and therefore the refraction distribution caused by the cornea.

Measuring devices are known, for the study of the refraction component of the optical system of the eye, which depend on spatial pupil coordinates. These include M. S. Smirnov's device for measuring the wave aberration [1], Van den Brink's device for measuring the transverse aberration [2], N. M. Sergienko's device for measuring the physiological astigmatism [3], and a spatially resolved refractometer [4]. The above devices, based on Scheiner's principle, involve point-by-point investigation over utilizing a number of optical techniques. However, in using all such devices the direct participation of the patient is needed in the preliminary aligning of the eye and in the aberration measurements.

More advanced measuring devices are known, which do not require the patient to act as a link in the "measurement chain". These include a device for measuring the aberration by the Foucault's knife method [5], a device for measuring the wave aberration using Hartmann-Shack sensors [6-8], including measurements that incorporate adaptive optics completely compensating the wave aberration [9].

Previously, existing devices did not incorporate means for providing an accurate reproducible "linkage" of the patient's eye to the spatial co-ordinates of the measuring device; they did not incorporate a means for adjusting the accommodation of the patient's eye that is necessary for studying the dependence of aberrations on the accommodation characteristics; they were not capable of taking measurements on a dilated pupil without using medicines.

Refraction can also be measured using a spatially resolved objective autorefractometer as disclosed in U.S. Pat. No. 5,258,791[10]. This device provides spatially resolved refraction data using a closed measuring loop which includes a reference pattern and a measurement beam. In this device, an origin of coordinates of the detector coincides with the center of the fovea image and the detector functions as a zero-position sensor.

BRIEF DESCRIPTION OF THE DRAWINGS

For a more complete understanding of the present invention, including features and advantages, reference is now made to the detailed description of the invention along with the accompanying figures in which like numerals represent like elements and in which.

DETAILED DESCRIPTION

Figure 1:
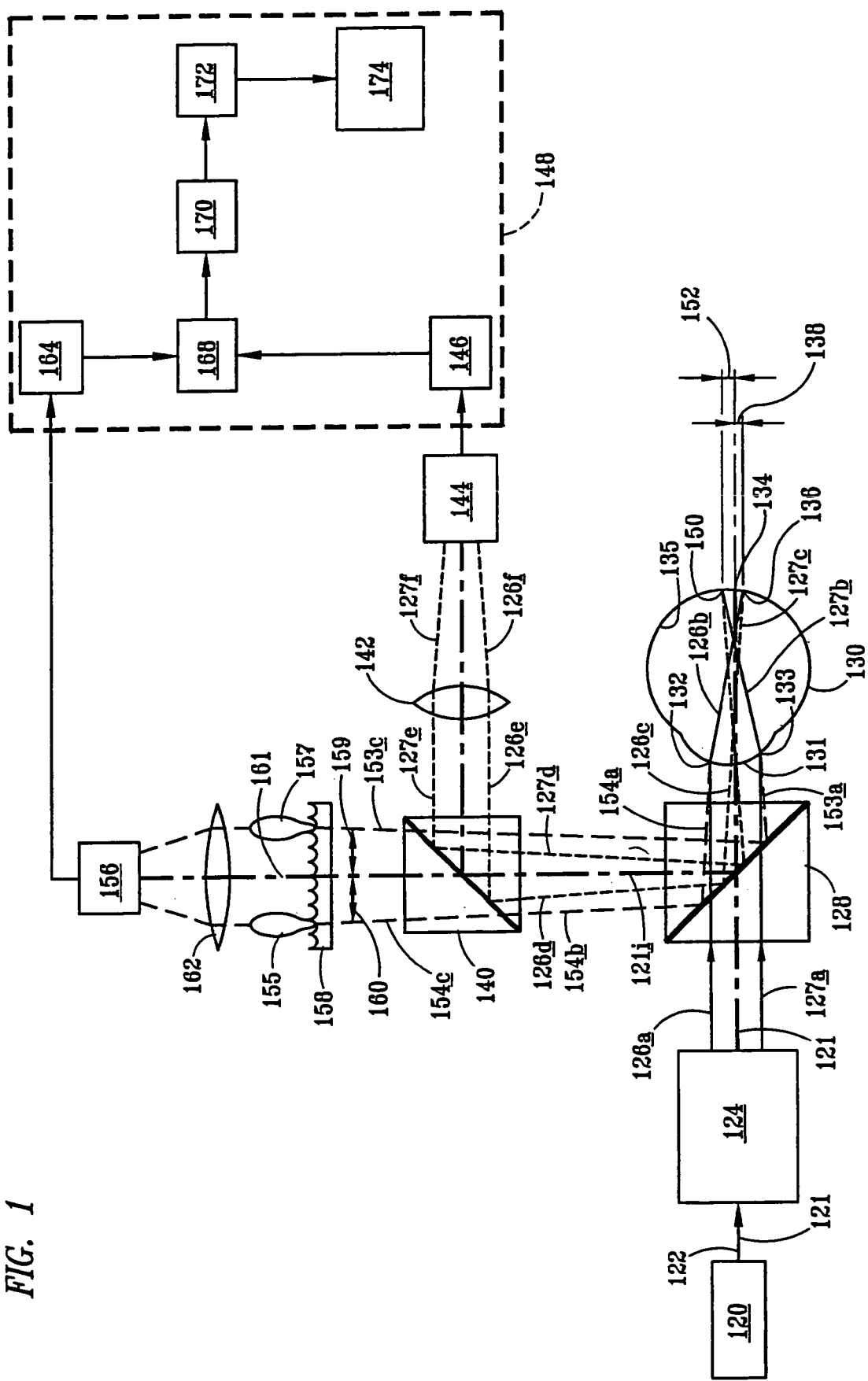
FIG. 1 is a functional schematic drawing a device for synchronous mapping of the total refraction non-homogeneity of the eye and its refractive components.

While the making and using of various embodiments and methods of the present invention are discussed in detail below, it should be appreciated that the present invention provides many applicable inventive concepts which may be employed in a variety of specific contexts. The specific embodiments discussed herein are merely illustrative of specific ways to make and use the invention and do not delimit the scope of the invention.

With the advent of modern methods for correcting total refractive errors of the eye and/or errors associated with the intraocular lens alone, it has become increasingly important to understand the physics of vision. The goal of "perfect vision" is an elusive one today. More often than not, perfect vision is obtained by chance and not calculation. New diagnostic instrumentation such as corneal topography have enabled today's ophthalmic surgeons to more greatly appreciate the detail and variability of the cornea's shape and hence its refractive power.

With the cornea providing roughly 70% of the refractive power of the eye it is a critical element, but not the entire picture. Better understanding of the corneal shape combined the subjective refraction measurements has lead to improved refractive surgery and intraocular lens exchange results. However, a more detailed understanding of the refractive errors associated with each element of the eye (corneal surface and internal optics) would provide improved outcomes for refractive surgery or intraocular lens exchange.

The input alone of the subjective refractive correction desired is by itself one of the largest errors in refractive correction procedure. It is certainly not an exact science, yet.

It has been discovered by Applicants that combining techniques for analyzing total aberration refraction of the eye and for analyzing cornea shape and its refractive contribution, whether synchronously measured or sequentially measured within a period of time, provides useful information on the contribution of each component of the eye. It has also been discovered by Applicants that measuring or determining the total aberration refractive and the refractive components of the eye under varying conditions of accommodation (both near point and far focal points), varying conditions of pupil constriction(both dark and light conditions)to find the visual function of the eye at boundary conditions, at conditions in between the boundaries and visual function response to dynamically changing conditions may provide additional useful information on the total refraction and the contributions of each component of the eye. Such information provides improved methods for correcting total refractive errors of the eye and/or errors associated with the intraocular lens rather than errors only of the cornea.

As with corneal topography, the keratometer is obsolete by a device that makes no assumption of sphero-cylindrical optics and describes point-by-point detail of the cornea's surface both within and outside the optical zone. With full appreciation of both optical and share characteristics of the cornea, keratometric analysis is rudimentary and only a crude summary of corneal optical performance. The time has come to look at the entire refraction of the eye and it's individual components with the same level of objective measure and detail. With this greater detail in analyzing the refractive status of the eye to include higher order aberrations as opposed to only sphere and cylinder, it will be possible to better understand and measure the quality of vision problems for patients. Predictably, in viewing a total refractive map of the eye, a refractive map of the cornea and a refractive map of the internal optics of the eye that colors the refractive power of these elements on a point-by-point basis as opposed to the basic total refractive numeric summary of sphere, cylinder and axis will have at least as much clinical impact as the corneal topography maps of the mid-1990's.

A method and a device for mapping the total refraction non-homogeneity of an eye are set forth in prior co-pending PCT Application No. PCT/US99/23327 (incorporated herein by reference), that includes directing into the eye a narrow light beam, its axis being parallel to the visual axis of the eye under investigation, scanning the beam over the eye aperture, receiving a portion of light back scattered by the retina, analyzing the position of the light spot projected on the retina, and reconstructing from the data a map of the total refraction of the eye. A discussion of the details of the total refraction non-homogeneity determination have been incorporated herein and certain aspects are set forth below.

Similarly, a method and device for determining and mapping the total refraction non-homogeneity of an eye are set forth in prior co-pending U.S. application Ser. No. 10/137,720 (incorporated herein by reference), that includes directing into the eye a narrow light beam, its axis being parallel to the visual axis of the eye under investigation, scanning the beam over the eye aperture, receiving a portion of light scattered by the retina, analyzing the position of the light spot projected on the retina, and reconstructing from the data, a map of the total refraction of the eye. Such map and results of the analysis described include sphere, cylinder, axis and higher order aberration contributions to the eye's total refractive error.

In many applications, information on the contribution of other refractive components of the eye may be helpful or necessary, as, for example, for subsequent corrective surgery.

It has been discovered by Applicants that marrying the techniques for analyzing retina-scattered light and for analyzing cornea reflected light gives very useful information on the contribution to the total eye refraction of such other refractive components of the cornea, and/or the eye lens, that has not heretofore been successfully accomplished.

A method for synchronous measuring the total refraction non-homogeneity of the eye and the corneal surface shape and refractive power is described in U.S. Pat. No. 6,409,345 (incorporated herein by reference). Described in that patent is a device for synchronous measuring aberration refraction of an eye. Calculation of the component of the total aberration refraction caused by the cornea has been accomplished with such a device comprising a light source producing a probing beam along a path to the eye. A beam shifter is provided to rapidly shift the probing beam to a plurality of spaced-apart parallel paths for impacting the eye at a plurality of points on the cornea. Backscattered light from the retina of the eye is directed onto a position-sensitive detector by which the total eye refraction is determined for each of the plurality of impingement points. Synchronized with each impingement point determination of the total eye refraction, there is a reflection from the impingement point on the cornea directed onto another position-sensitive detector for determining the refraction component caused by the cornea. A comparator can synchronously compare the total refraction for each impingement point to the component of refraction caused by the cornea and by appropriate calculations can determine the component of refraction caused by the components of the eye other than the cornea. the corneal component is effectively extracted or "subtracted" from the total refraction component. The data can be placed in memory and/or can be supplied to a program device for map reconstruction, to a representative display of the refraction characteristics of the eye and its components, or to a lasik surgical instrument or other cornea shaping device or corrective lens (glasses or contacts) shaping device for vision correction.

In one embodiment a device for synchronous measuring aberration refraction of an eye and calculation of the component of the total aberration refraction caused by the cornea has been accomplished with a device comprising a light source producing a probing beam along a path to the eye as set forth in U.S. Pat. No. 6,409,345. A beam shifter is provided to rapidly shift the probing beam to a plurality of spaced-apart, parallel paths for impacting the eye at a plurality of points on the cornea. Backscattered light from the retina of the eye is directed onto a first position-sensitive detector by which the total eye refraction is determined for each of the plurality of impingement points. Synchronized with each impingement point determination of the total eye refraction, there is a reflection from the impingement point on the cornea directed onto a second position-sensitive detector for determining the refraction component caused by the cornea. A comparator synchronously compares the total refraction for each impingement point to the component of refraction caused by the cornea and by appropriate calculations (as by "subtraction" of one component from the other component on a point by point basis, a by surface by surface basis, a wave front by wave front basis or otherwise) determines the component of refraction caused by the parts of the eye other than the cornea. The primary component contributing to eye refraction is the intraocular lens (IOL). In many instances it may be assumed with high accuracy that the entire component of refraction other than the cornea will be a result of the IOL. This data can be placed in memory, can be supplied to a program device for map reconstruction and to a representative display of the refraction characteristics of the eye and its components, and or can be used in conjunction with vision correction techniques, such as for programming lasik surgery or other ablation devices or for forming corrective lenses, glasses or contacts or implantable intraocular lenses.

In another embodiment a device for measuring total refraction and a device for measuring corneal topography are combined by coordinating the eye aperture to provide point by point registration or alignment, converting wave front aberration and corneal topography to consistent formulations. For example, both sets of data may be calculated in terms of wave front mapping, both may be calculated in terms of topography, both in terms of optical path length (OPL) differences for spatially resolved points of the eye, deviations from a theoretically correct eccentric hyperbolic function or otherwise. The component not contributed by the corneal topography is then extracted, as if by "subtracting" the corneal component of the refraction data from the total aberration data. With this method, the refractive contributions of the cornea and the refractive contributions of the lens or portions of the eye other than the cornea, are determined.

For additionally improved resolution, a program device may be provided for inserting an additional measuring point or impingement point located between neighboring measuring points that produce a different value higher than a specified maximum difference threshold.

Thus, an object of the present invention is to provide an improved combination for measuring the aberration refraction of the eye. In one embodiment, an aberration refractometer allows estimates of the ametropy, astigmatism characteristics, and simultaneously allows synchronous determination of component parts of total aberration refraction of the eye contributed by the cornea and therefore the components contributed by other portions of the eye. This embodiment thereby allows visual acuity and increased accuracy of calculations of the part of the cornea to be removed by photorefractive keratectomy [11] or lasik surgery, if necessary to correct eye refraction non-homogeneity or aberration. Current standards can be used by generating a wavefront error 3D map and building a tissue removal program off of the cornea surface to ablate enough tissue on a micron by micron basis to fit the wavefront error map according to the characteristic patterns generated by a specific laser. The ablation may be for purposes of correcting the corneal component only, and custom formed intraocular lens may be used to correct the component not attributed by the cornea and therefore deemed to be primarily a component of error caused by the lens.

In other embodiments the entire correction may be provided either at the cornea or at the lens. However, because of the offset between the plane of the cornea and the plane of the lens (see FIG. 14) the amount of ablation at each point on the cornea is adjusted, or the form of the lens is adjusted, to compensate for the difference that results from the relative offset positions of the cornea and the lens. Thus, by knowing which portion or the aberration is actually caused by which component of the eye corrections applied either at the cornea or at the lens can be made to more accurately provide vision correction.

It has also been found that, although there may be some noncoincidence of the points of primary information from attempted combination of total eye refraction information and the surface shape of a cornea, maps reconstructed from such cornea topography data and separately obtained total eye refraction aberration data can be aligned or otherwise registered with each other to avoid significant errors when reconstructing the differences. A workable device and method for mapping of the total refraction non-homogeneity of the eye, mapping the refraction components of the cornea and determining from the total refraction map and the corneal topography map, the refraction components caused by the lens or other contributors to the total refraction would be desirable.

In one embodiment, the aberration refractometer comprises a light radiation source, preferably laser light or other polarized light; a telescopic system; a two-coordinate deflector consisting of two single-coordinate deflectors; a deflection angle control unit; an aperture stop; a field stop; a collimating lens; an interferential polarizing beam splitter; a first position-sensitive photodetector with an objective lens for detecting only the position of light backscattered from the retina; a second photosensitive photodetector with an objective for detecting only the position of polarized light reflected from the cornea; a comparator for point-by-point comparison of the retinal backscatter position and the cornea reflection position; and a data processing and display unit consisting of a computer, an analog-to-digital converter and a preamplifier.

In another embodiment the beam of light is not laser light and not polarized. For example a high intensity beam of light produced by a super luminescent radiant diode as the light source. A telescopic system; a two-coordinate deflector consisting of two single-coordinate deflectors; a deflection angle control unit; an aperture stop; a field stop; a collimating lens; a position-sensitive photodetector with for detecting the position of light backscattered from the retina; a photosensitive photodetector for detecting the position of polarized light reflected from the cornea; a computer program for receiving the photodetector data and for using an algorithm to separate high intensity light reflection at a point of the corneal reflection, from lower intensity light reflected back from the retina. The algorithm may for example determine the light having an intensity greater that n a certain value is reflected from the cornea and light having a lesser intensity construed as light back scattered from the retina. points with light reading s outside of a normal intensity for high intensity light reflected from the cornea can be disregarded, without seriously interfering with the accuracy of the total model. One photo detector may be sufficient or two or more than one photo detectors may be used with an appropriate algorithm for separating the component reflections and for disregarding the relatively infrequent anomalous data points.

An instrument of the present invention employing ray tracing technology is able to reduce the time needed for measuring the refraction, eliminate light beam energy losses at the aperture stop and create a flexible system for locating the measurement points on the pupil by providing the following: the telescopic system is positioned in the probing beam path after the two-coordinate first deflector at a distance corresponding to the coincidence of the entrance pupil of the telescopic system and the gap or zone between the single-coordinate deflectors, the aperture stop or diaphragm is placed between the lenses of the telescopic system at the point of coincidence of their foci, and the field stop or diaphragm is positioned in the plane of the exit pupil of the telescopic system and, at the same time, at the location of the front focus point of the collimating lens situated in front of the interferential polarizing beam splitter at such a distance from the patient's eye which is approximately equal to the focal distance of the collimating lens.

To ensure a constant optical coupling of the photosensitive surface of the first photodetector and the retina for both emmetropic and ametropic eyes, a group of lenses with variable optical power is installed between the interferential polarizing beam splitter and the eye, said group of lenses having the function to adjustably form the retina image of an ametropic eye at infinity regardless of the emmetropic or ametropic condition of the eye. The photosensitive surface of the first photodetector is conjugated with the front focal plane of the objective lens, being inserted following the interferential polarizing beam splitter on the path of the light scattered by the retina.

To provide for fixation of the patient's line of sight along the optical axis of the instrument and to compensate for accommodation of the eye at the required distance while keeping constant optical conjugation of the patient's eye with the photosensitive surface of the detector, a second beam splitter or an optical axis rotation mirror, as well as a plate with a gaze fixing test pattern or a test-target for sight fixation are optically coupled with the photosensitive surface of the photodetector and are located between the photodetector and the objective lens. A second optical group of lenses, with variable negative optical power and which function to form an image for the patient's eye of the test-target at a distance corresponding to the preset accommodation, is positioned between the second beam splitter or optical axis bending mirror and the interferential polarizing beam splitter. When an optical axis bending mirror is used, it is mounted on a movable base making it possible to displace the mirror so as to enable the light radiation scattered by the retina to reach the photodetector during the measurement of the patient's eye characteristics.

In one embodiment, to account for systematic refraction measurement errors, a second mirror, for bending or redirecting the optical axis of the probing laser beam is inserted in the laser beam path after the last optical element before entering the patient's eye. Following the second mirror, an optical calibration unit for simulating an eye is inserted. The optical calibration unit includes an axially movable or stationary retina simulator whose optical characteristics are equivalent to those of the human retina. The second optical axis bending mirror is installed on a movable base so that it can be moved into the probing laser beam path during measurement with the optical calibration unit and moved out when measuring the patient's eye refraction.

To align the instrument relative to the patient's eye as well as to enhance accuracy and enable automation of the aligning process, the instrument is provided with a third beam splitter to insert a channel for eye alignment verification of the instrument and the patient's eye. In a preferred embodiment, the co-axial verification channel comprises one or more point of light sources and a TV or electro-optic detecting device, together serving to display the pupil and/or eye image and providing a permission channel to measure eye characteristics when the optical axis of the instrument and the visual axis of the patient's eye coincide. To enable the instrument to be used without dilating the pupil with a medicine, a laser radiation source and/or infrared light sources are incorporated into the coaxial verification alignment mechanism. It is contemplated that the instrument can be used to make refraction measurements under conditions simulating either day or night light conditions.

In an alternate embodiments it is further contemplated that the alignment verification can be done under the control of the operator of the device or can be automated. In one embodiment, the co-axial verification channel provides either visual or acoustic notification that coincidence between the instrument optical axis and the patient's visual axis is proximate or near to "on target" status. Once this status is attained, the instrument is "armed" electronically. Once full coincidence is attained, the measurement controller automatically causes spatially defined parallel light beams, preferably laser beams, to be rapidly fired and enter the eye through the input channel. Light reflecting from the retina is directed to the retinal spot detecting channel for spatial and intensity characterization. This process can permit upwards of at least 5 replicate measurements over 65 spatial locations to be taken within 15 milliseconds without the need for the patient to actively participate in the targeting and alignment process.

FIG. 1 shows a schematic functional view of a device and method for synchronous mapping of the total refraction non-homogeneity and components thereof according to one aspect of the present invention. A polarized light source 120 and preferably a laser light source directs a light beam 122 along a light beam path nominally coincident with a central eye axis. The light beam is provided to a beam shifter 124 that is controlled to rapidly shift light beam 122 to any of a plurality of spatially offset parallel light beam paths 126. The mechanism for light beam shifting will be discussed more fully below in connection with FIGS. 3 and 4. Beam shifter 124 provides a probing beam 126. It will be understood that a plurality of such probing beams can be produced by beam shifter 124 within a few milliseconds as, for example, five passes of 65 spatially offset parallel probing beams can be produced within 12 milliseconds, or two passes of 255 spatially offset parallel probing light beams can be produced within 200 milliseconds. For example, only one of the probing beams may be coincident with central axis 121, another of the plurality of offset polarized probing is depicted as 127. It will be understood that, for purposes of clarity, the 65 or more parallel polarized probing beams are not depicted in FIG. 1. Each of the probing beams 126, as well as the plurality of beams 127, pass through a beam splitter 128 to the eye 130 under investigation. Each probing beam 126, 127 impinges upon the cornea 131 at a plurality of impingement points as, for example, point 132 corresponding to probing beam 126 and impingement point 133 corresponding to probing beam 127, is representative of a plurality of impingement points.

The total refractive eye aberration for a thin beam of light entering at impingement point 132 is determined by locating point 136 on the retina and determining the spatial position 138 of that illuminated point on the retina 136 relative to the fovea 134 aligned along central axis 121. This position may be indicated relative to central axis 121 by coordinates ($dx_1$, $dy_1$). Light impacting the retina is backscattered off the retina. One method of determining which light reflects from the retina and which reflects form the cornea is to use the concept that the backscattering from the retina is not a reflection per se and therefore by using a polarized probing beam, the entering beam 126b is depolarized by the retinal surface. The backscattered light, having its optical axis represented by path 126c, is non-polarized light. The light 126c is directed in beam splitter 128 along path 126d to a polarizing beam splitter 140. Beam splitter 140 is a polarizing beam splitter so that it reflects non-polarized light and allows polarized light to pass through it. Thus, beam 126d is directed along path 126e through a lens 142 that focuses it along path 126f to a first photo detector 144. As will be discussed more fully below with respect to FIGS. 2, 3 and 8, photo detector 144 may be provided with a further beam splitter 94 and x and y photodetection arrays 88 and 89 to determine the position ($dx_1$ and $dy_1$). From this position and based upon the standard length of the eye, the total refraction characteristics can be calculated in a total refraction calculator 146. The total refraction calculator 146 may, for example, be circuitry and/or computer software within a multifunction computer 148.

Returning now to FIG. 1, each of the plurality of offset probing beams of which 127a is a sample, passes through beam splitter 128 and impinges upon the anterior surface of the cornea 131 at a plurality of impingement points of which 133 is a representative sample. Entering at impingement point 133, the beam 127b is projected due to the total refractive characteristics of the eye along the path of beam 127 to a point 150 on the retina 135 of eye 130. The backscattered light 127c from the retina 135 is projected back out through the eye aperture and is directed by beam splitter 128 along path 127d to the polarizing beam splitter 140, where it is directed along path 127e through lens 142 and onto a first photodetector 144 for determining the offset location 152 represented by ($dx_2$, $dy_2$) away from central axis 121. Through the rapid and repeated operation of beam shifter 124, a plurality of times within a fraction of a second, an entire grid pattern of impingement points, see, for example, the grid pattern of FIG. 10. As will be more fully discussed below, mappable data, with respect to the total eye aberration Is provided at the total refraction calculator 146.

Synchronously with each of the polarized probing beams 126a and the plurality of additional beams 127a, the component of aberration caused by aberrations in the cornea surface 131 may simultaneously be determined. Because beams 126a and 127a are polarized light, they will partially reflect off of the cornea surface 131 as a polarized light beam 154a, in the case of probing beam 126a, at an impingement point 132 and as reflected polarized light 153a in the case of probing beam 127a and at impingement point 133. Because the light reflects from the cornea at an angle corresponding to the angular position of the anterior cornea surface 131 at the point of impingement 132, reflected beam 154a diverges from beam 126a, depending upon the refractive characteristics of the cornea 131 at the impingement point. Beam 154 is directed by beam splitter 128 to polarizing beam splitter 140 along path 154b. The beam 154b passes through polarizing beam splitter 140 because it is polarized light that was reflected from the cornea surface and travels along path 154c so that its position may be detected by a second photodetector 156. To facilitate determination of the reflective angle of beam 154 off of the cornea, the distance from the cornea to a semitransparent scattering screen 158 is a known quantity so that the offset distance 160 of the beam 154c impacting scattering screen 158 is indicative of the topography of the cornea surface 131.

The scattering screen 158 causes, the light beams 154c and 153c, to scatter, as schematically depicted with scattering diagrams 155 or 157. The position 160 or 159, with respect to the optical centerline 161, is imaged by a lens 162 onto the second photodetector 156. Once again, the second photodetector 156 may comprise an array of x and y photodetectors using a beam divider to determine the x-y position 160 for the reflected light from the cornea. This information is provided to a cornea cause refraction calculator 164.

The data from both total refraction calculator 146 and from he cornea cause refraction calculator 164 is fed into a comparator 168 and also to memory 170. The comparator information produces data, including the total refraction for each point, the cornea cause refraction for each impingement, i.e., for each shifted probing beam and may also determine the component of the refraction aberration due to components of the eye other than the cornea. From this information, a map of refractive characteristics of the eye is reconstructed in a map reconstruction unit 172. The reconstruction map produced at 172 may be displayed at a display 174, such as a CRT screen or a color printout. All of the total refraction calculator 146, the cornea cause refraction calculator 164, the comparator 168, the memory 170, the map reconstruction unit 172 and the display 174 may be separately provided or alternatively may be included in a computer system and display screen and/or printer schematically represented by system dash lines 148 in FIG. 1.

Figure 2:
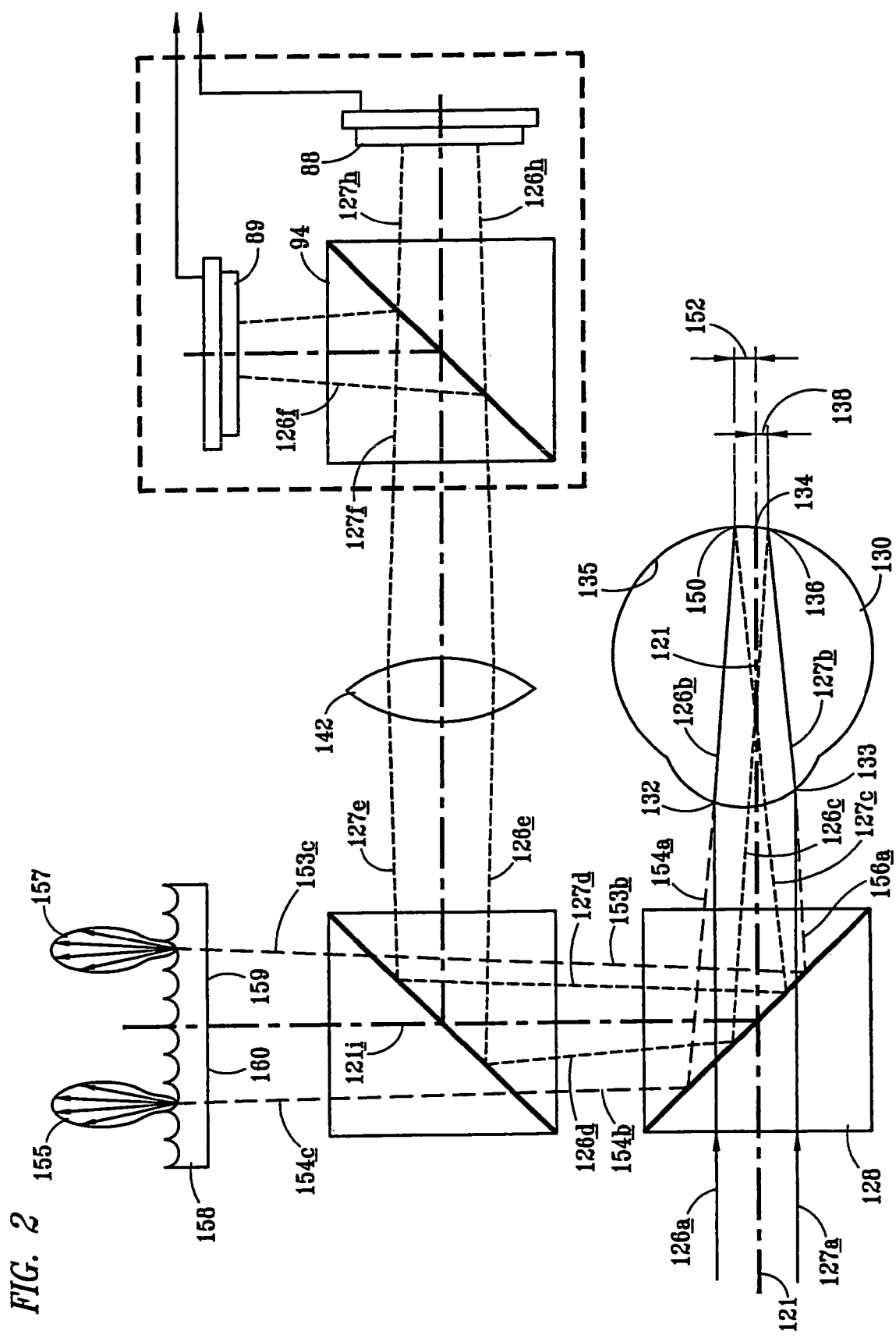
FIG. 2 is a schematic depiction of an eye under investigation in which the theoretical aspects of the total eye refraction determination and also the corneal component of refraction may be more fully understood.

FIG. 2 is an enlarged schematic view of a portion of the device for synchronous mapping of the total refraction and its component parts, better schematically depicting the paths of the probing beams 126a and 127a, as well as the backscatter light path 126c, 126d, 126e and 126f to a photodetector 146. The photodetector 146 is shown comprising an x component detector 88 and a y component detector 89. Further, the beams respectively directed or passing through the polarizing beam splitter 140 are more clearly depicted and the points of impingement on the semitransparent light scattering screen 158 are more clearly demonstrated.

The semitransparent light scattering screen 158 may, for example, be milk glass or translucent fluorescent light cover material having a substantially homogeneous characteristics so that polarized light beams impacting at any point produce the same relative intensity and same relative diffusion by which the position of such light beams may be detected with position sensor 156. The second position sensor 156, although not depicted, may also be constructed similarly to position sensor 146 so that x component sensor array 88 and y sensor component array 89 are used in combination to get an x-y position sensor.

Figure 3:
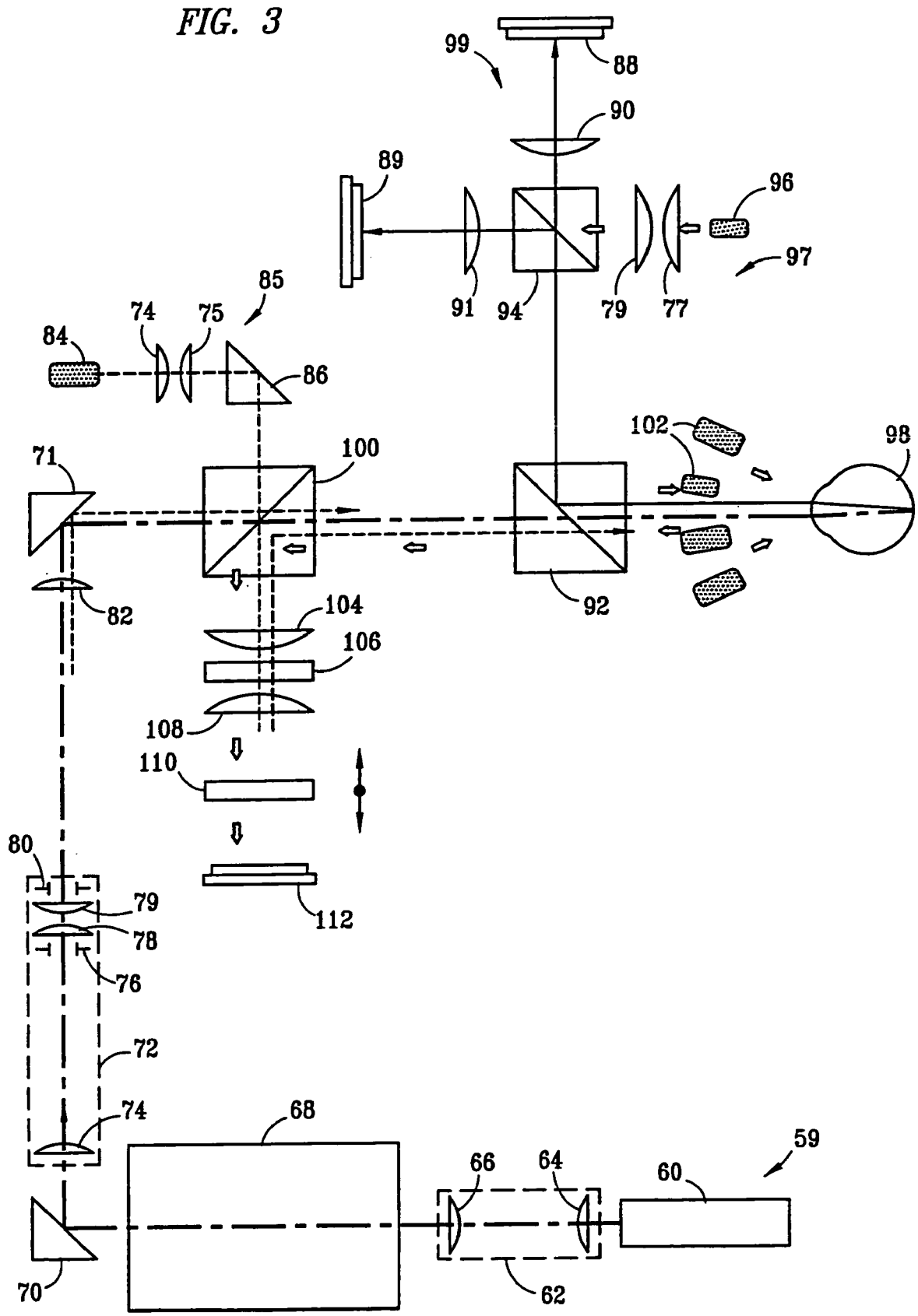
FIG. 3 is a schematic diagram of a preferred alternative embodiment of an aberration refractometer according to certain aspects of the present invention.

FIG. 3 schematically depicts the optical channels of one embodiment of the total aberration portion of the refractometer of the subject invention. A spatially defined parallel beam input channel 59 extends from a light source such as a laser or other low diffusion light source up to the eye of a patient 98. In one preferred embodiment a 650λ laser was employed. Along the spatially-defined parallel beam input channel is a cylindrical telescope 62 including two lenses 64 and 66. Light from the cylindrical telescope enters the deflector 68. The deflector 68 is preferably an acousto-optical deflector electronically controlled by a control unit such as a computer. Alternatively a galvanometric mirror deflector or the like could be used. Two coordinate deflectors or angular direction mechanisms may be used as a deflector 68. A reflection mirror or mirror prism 70 reflects the light beam through a telescopic system 72, including preferably, but not necessarily, a lens 74, an entrance aperture 76, lenses 78 and 79 and an exit aperture or field stop 80. The polarized light beam passes from the field stop 80 to collimating lens 82 and is deflected by mirror 71 and passes transparently through beam splitter 100 and interferential beam splitter 92 en route to the eye 98.

Light sources placed in front of the eye are used to align the visual axis of the eye with the optical axis of the instrument. Preferably a plurality of orthogonally placed light emitting diodes (LEDs) 102, for example emitting at a X of 940 mm could be employed. Light produced by LEDs 102 is reflected off the cornea and imaged by camera 112. When the reflected light aligns with preset targeting parameters, the instrument is in the proper alignment and therefore in the permissive mode for firing of the spatially resolved parallel beams formed along channel 59.

The illuminated eye is then ultimately imaged by camera 112 as the image passes through the beam splitter prism 92 and is redirected at beam splitter 100 to pass through optical elements 104, 106, 108 and 110 to finally fall upon the CCD camera 112.

A retinal spot position detecting channel 99 is used to detect the position of reflected spots from the retina of eye 98 created by the input channel and includes a interferential polarization beam splitter 92 that directs non-polarized reflected light from the retina of eye 98 to a position sensor.

In one embodiment of a photodetection position sensor as shown in FIG. 3, there is a beam splitter 94 that splits the image directing one component of the nonpolarized retina image through an optical lens 90 to a "x-coordinate" photodetector 88 and directs another component of the image through optical lens 91 to a "y-coordinate" photodetector 89. Preferably, the orthogonally placed photo detectors 88 and 89 are high resolution linear array photodetectors and the position measurement created on those detectors may be used directly to provide XY coordinates for the measurement of the position of reflected spots on the retina of eye 98. Instead of using linear array detectors, an actual XY matrix photo detector or a CCD detector with its own objective lens can be used to replace the beam splitter 94 lenses 90 and 91 and the linear array photodetectors 88 and 89. One benefit of the linear arrays is that they provide for a large range of aberration detection that exceeds the range of a simple quadrant photodetector. For example, a typical quadrant photodetector may be useful for detecting aberrations of a range of about ±3 diopters while linear arrays can accommodate a range of approximately ±10 diopters. Another option is to use lateral position sensing detectors. The drawback of using a quadrant detector is in the dependence on the shape and size of the light spot imaged on its surface. Multi-element detectors like 1D or 2D arrays (linear arrays or CCD) as well as lateral position sensing detectors are free of this drawback. In yet another embodiment, the photo detector may be a 2-dimensional or x-y photodetection matrix or a CCD sensory matrix.

Figure 11:
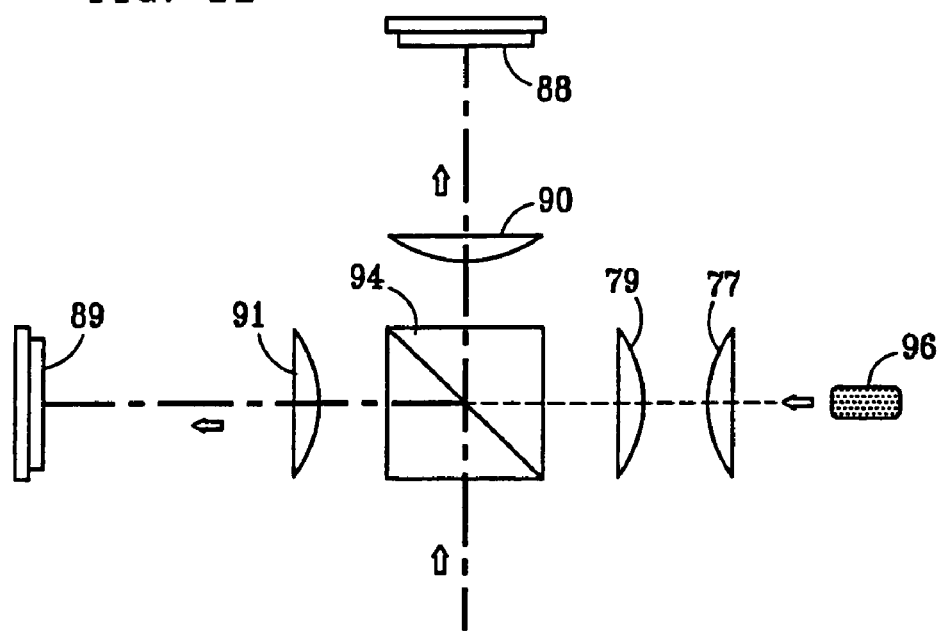
FIG. 11 is a schematic illustration of a photodetector using linear array detector components.

Details of the embodiment depicted in FIG. 3 are further explained with reference to FIG. 11 below. The position of a spot of targeting light reflected back from a reflection spot on the fovea of the retina can be determined using reflection beam splitter 94 to direct a first portion of the reflected nonpolarized light from the retina spot through lens 90 to an x-direction linear array photodetector 88 for measuring changes in position only in one direction, for example in a x-direction. A second portion of the reflected nonpolarized light, substantially identical to the first portion, is directed through lens 91 to a y-direction linear array photodetector 89 for detecting changes in nosition only in a direction at ninety degrees to the first direction, for example the y-direction. The change in the x-y position is measured by calculating the position of the center of light intensity of the light spot projected on the linear array 88 (x direction) and linear array 89 (y direction).

Light source 96 and condenser lenses 77 and 79 enable homogeneous irradiating of the linear arrays 88 and 89, thus checking their homogeneity at servicing. Light emitting diode 96 and condenser lenses 77, 79 form a wide beam for calibrating photodetectors 88 and 89. If any of the elements is out of tolerance, its output can be corrected at signal processing procedures.

A fixation target channel 85 preferably comprises a light source. In a preferred embodiment the light source is a green 565λ LED 84. The light may be transmitted through lenses 74 and 75 and directed by prism 86 and through beam splitter 100 which has wavelength differentiating optical coatings. Fixation target is positioned on the optical element 106. The light beam from LED 84 passes through lenses 104 and 108 and fixation target 106 and is reflected off of the mirror 110. The fixation target light passes back through the lens 104 and is redirected by beam splitter 100 at 90 degrees out toward the eye for the patient to visualize the image as coming from the location of the surface 110 which image can be moved from near fixation to far fixation or adjustable anywhere in between and this may be used for changing the eye accommodation over a period of time and simultaneously taking a series of measurements including spatially resolved aberration refraction measurements as well as pictures on the CCD camera 112. This produces a time lapse imaging of the eye and measurements of the aberration refraction as it cycles through different fixation target distances. The different target fixation distances may be automatically moved or adjusted from near to far using electro mechanical adjustment means that may be synchronized with the measurements and/or images taken on a time lapse basis.

The instrument described herein was developed to provide a total aberration refractometer able to accurately and quickly provide a refractive map of either emmetropic or ametropic eyes without accommodation error.

Figure 4:
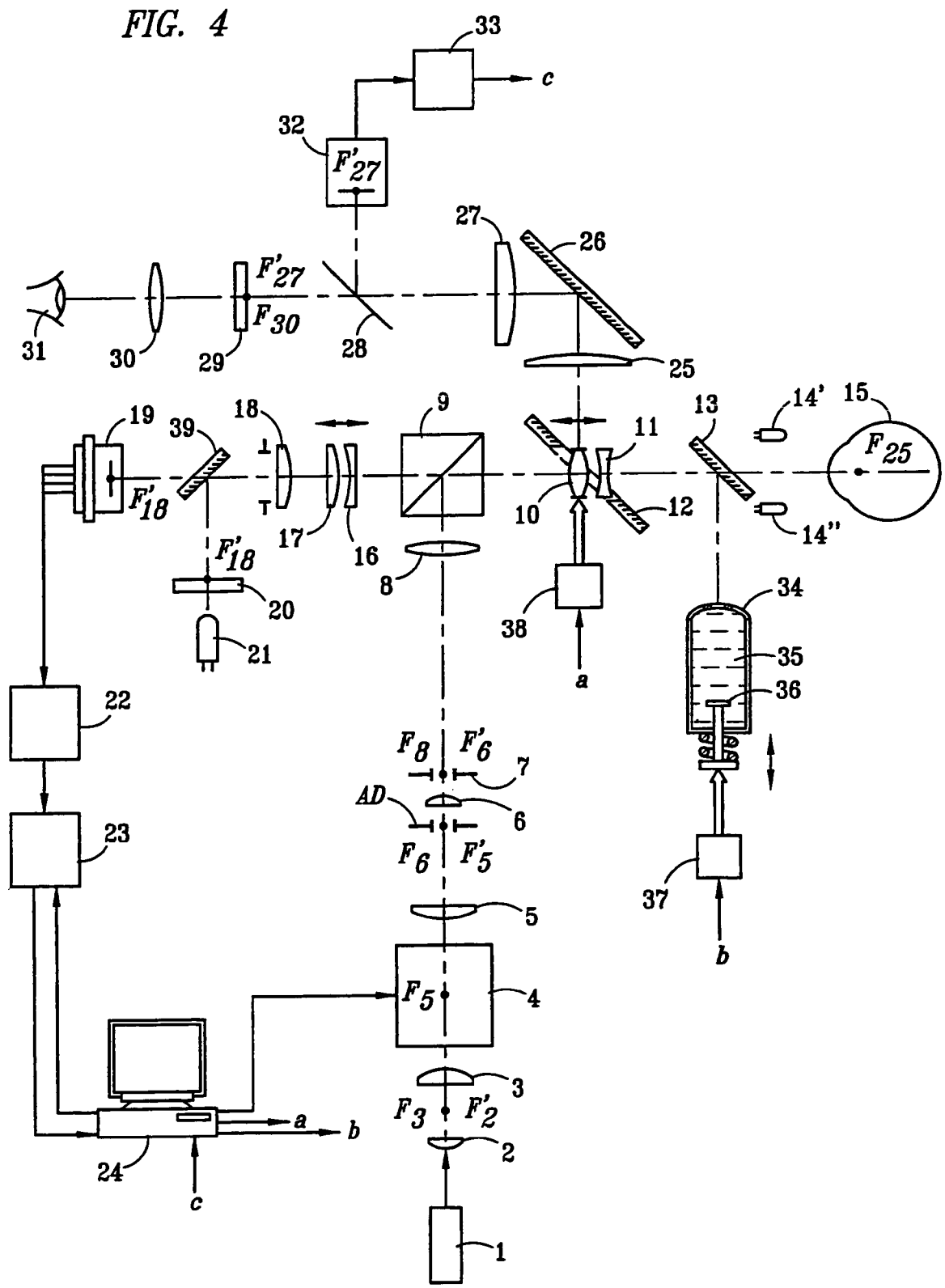
FIG. 4 is a functional schematic diagram of an instrument for measuring total aberration refraction.

FIG. 4 shows a functional diagram of another embodiment of the subject instrument for measurement of the total aberrations in the eye and total refraction non-homogeneity. A light source whose radiation is used for the ray tracing of the eye is provided, as for example, by laser 1. A telescopic expander comprising for example lenses 2 and 3 provides a normal functioning of a two-coordinate acousto-optic deflector 4 preferably consisting of two single-coordinate deflectors. A telescopic laser-beam narrower is formed by lenses 5 and 6 with an aperture stop or diaphragm AD located at the common foci of the lenses 5 and 6. A field stop or diaphragm 7 is placed at the back focus of lens 6 so that its image formed by the telescopic narrower in the back-pass is located between the single-coordinate deflectors. With this placement, the redistribution of the light illuminance in the light spot on the pupil is minimized when the angular position of the laser beam is varied at the exit of the single-coordinate deflectors. The front focus of a collimating lens 8 is aligned with the center of the field stop or diaphragm 7 to ensure telocentric passage of rays through interferential polarizing beam splitter 9.

An ametropia compensator is schematically depicted as a varifocal group of lenses 10 and 11, adjustable to compensate for the patient's eye ametropia. One of the lenses is mounted on a movable base connected to actuator drive 38. An accommodation controller is schematically depicted as lenses 16 and 17 that constitute a varifocal group of lenses for accommodation control of the patient's eye.

An objective lens 18, at whose focal point the photosensitive surface of a position-sensitive photodetector 19 is located, is intended to form an image of the irradiated retina in the plane of the photosensitive surface of the position-sensitive photodetector. The photosensitive elements of the photodetector are connected through a preamplifier 22 and an analog-to-digit converter 23 to a computer 24. A beam coupler 39 is movably mounted between the objective lens 18 and the photodetector 19 to optically conjugate the plane of the test-target or plate 20 with the photosensitive surface of the first photodetector 19 as well as with the fovea surface. The plate 20 is needed to ensure the fixation of the patient's gaze. Located behind the plate 20 is a light source or radiator 21 serving to illuminate the plate.

Elements 25 through 30 comprise a microscope whose objective lens consists of lenses 25 and 27 together with mirror 26. A plate 29 with first coordinate-grid is preferably located at the back focal plane of a lens 27. A lens or a group of lenses 30, the front focal point of which coincides with the back focal point of the lens 27, comprises an eyepiece of the microscope. The beam splitter 28 serves to optically couple the retinal plane with the photosensitive plane of a TV camera 32 connected to the computer through a video signal conversion and input board, alternatively termed a frame grabber board, 33.

By means of a mirror 12 provided with an opening, the optical axis of the microscope is aligned with the optical axes of the ray tracing channel (elements 1-11) and the photoelectric arrangement for measuring the transverse ray aberration on the retina (elements 16-19).

In a preferred embodiment, four light-emitting diodes (LEDs) 14 are installed in a cross-wise configuration in front of the patient's eye. Each LED is preferably located in the same plane as each other LED, at an equal distance from the optical axis and perpendicular with the axis. The microscope and the LEDs comprise a system for the visual and television positioning of the instrument relative to the patient's eye. The microscope is installed so that the front focal plane of lens 25 coincides with the plane, where imaginary or virtual images of the LEDs 14, mirrored by the anterior corneal surface, are located.

Before the total refraction measurement process is commenced, the instrument is positioned relative to the patient's eye and the instrument is calibrated using the optical calibration unit 34-36. Movably mounted between the lens 11 and the LEDs 14 is a mirror 13 which serves to join the optical axes of the instrument and the optical calibration unit 34-36. In one preferred embodiment of an optical calibration unit, it comprises a meniscus or cornea simulator 34, liquid medium or vitreous simulator 35, and retina simulator 36. The retina simulator 36 is preferably movably mounted so that it can be moved along the optical axis by means of actuator or drive 37.

The instant measuring instrument incorporates a computer 24 or like device for controlling the acousto-optic deflector 4, analog-to-digital converter 23, and actuators or drives 37 and 38. The computer 24 or like device or devices may perform additional duties including, for example, mathematical processing and data storage, calculation and display of aberration parameters and the ocular refraction characteristics as well as provide setting measurement modes and implementation of automatic instrument alignment.

The instrument for measurement of the total eye refraction, in its preferred embodiment, functions in the following way. The light beam emitted, for example by laser 1, is expanded, collimated and directed to the acousto-optic deflector 4, which changes its angular position in accordance with the corresponding computer program. The telescopic narrower 5 and 6 reduces the beam thickness to the requisite magnitude. The center of the stop or diaphragm 7 is a point of angular "swinging" of the beam exiting from the telescopic narrower. Due to its positioning in the front focal plane of the lens 6, the aperture stop or diaphragm AD has its image in the back focal plane of the lens 8 which is aligned with the eye pupil. Further, because the stop or diaphragm 7 is positioned in the front focal plane of the collimating lens 8, angular swinging of the laser beam with the angle vertex located on the stop or diaphragm 7 is converted into parallel shifting of its optical axis after passing the lens 8.

If the patient's eye is ametropic, the axial movement of the lens 10 (or 11) converts the telocentric beam into a beam which diverges (in the case of myopia), or converges (in the event of hyperopia), so that the image of the diaphragm 7 is optically conjugated with the retina. This also ensures parallelism of the rays reflected by the retina in the zone in front of the beam splitter 9., which is necessary for its normal functioning.

The light entering the eye 15 of the patient is polarized in the plane shown in FIG. 4. Only that component of the returning beam depolarized by interaction with the retina is allowed by the beam splitter 9 to pass to the first photodetector 19. This protects the first photodetector from the polarized light reflected by the surfaces of the lenses 10 and 11 and by the cornea or the eye and which can produce an illuminance incompatible with determining the total refraction according to normal functioning of the instrument.

Lenses 16 and 17 and the objective lens 18 produce an image of the illuminated area of the retina in the plane of the first photodetector 19. In FIG. 4 the foci locations are designated as follows: $F_3$, $F_5$, $F_6$, $F_8$, $F_{25}$, and $F_{30}$, designating points of front foci of the corresponding lenses while $F_2'$, $F_5'$, $F_6'$, $F_{18}'$, and $F_{27}'$, designating points of back foci of the lenses.

Figure 5:
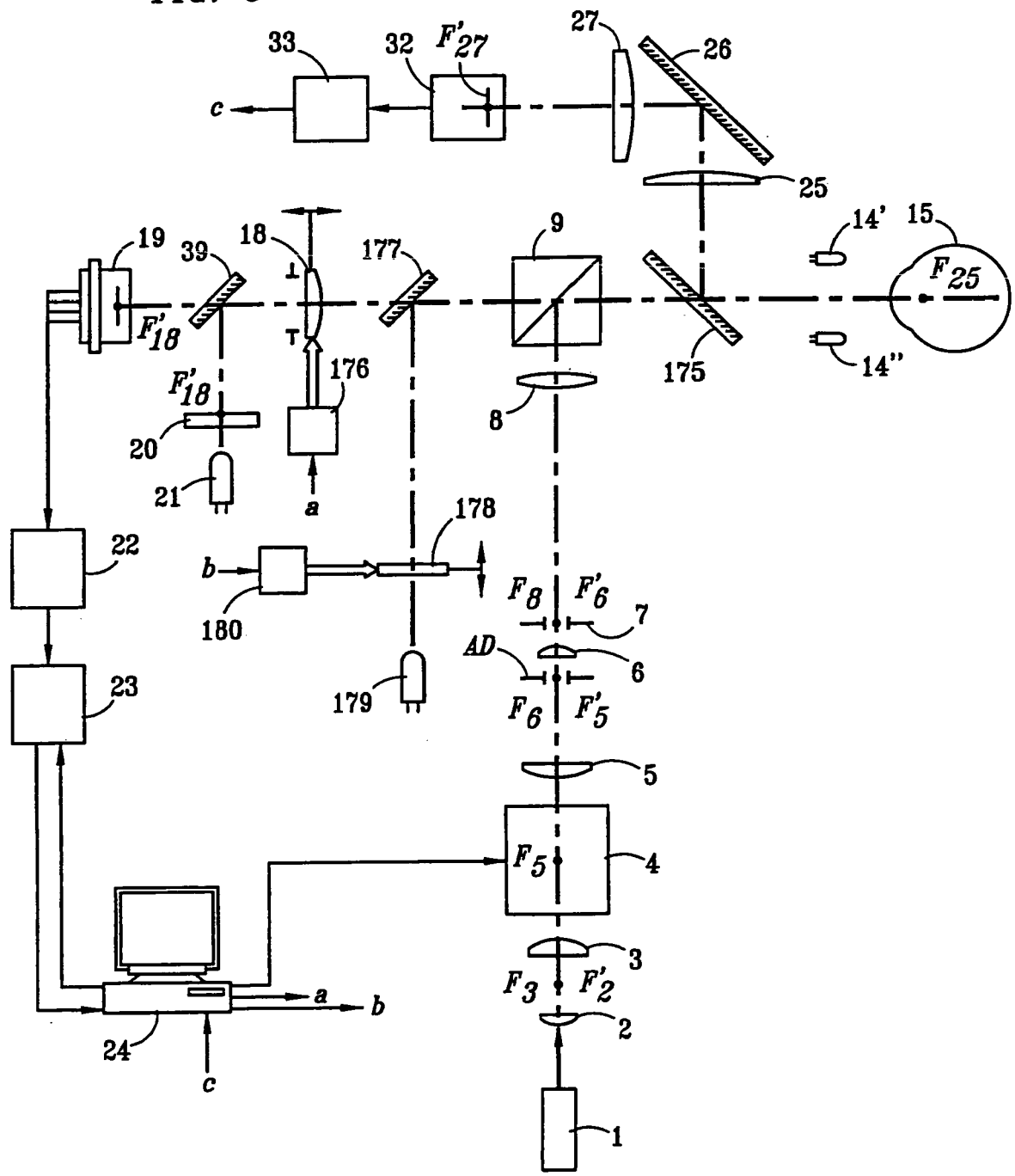
FIG. 5 is a schematic illustration of the operation of one embodiment of a device for measuring the total transverse aberration of a laser beam on the eye retina.

In one more embodiment, presented in FIG. 5, the function of ametropia compensator is combined in the component 18 that is an objective lens for the photodetector 19. In this embodiment, target object 20 and photodetector 19 are positioned at equal distances from the lens 18. LED 21 irradiates the target object 20. The lens 18 is positioned by the patient in such a way that a clear image of target object 20 is seen. In this position, focal planes of the photodetector 19 and the eye 15 are conjugated. Positioning of the lens 18 can be implemented with the electric drive 176. This positioning can be done automatically. Accommodation control is executed with another target object 178, irradiated by the LED 179, and positioned by an electronic drive 180. Both drives, 176 and 180, are connected with computer 24. Accommodation target object 178 is coupled with optical axis by the mirror 177. Colors of LEDs 21 and 179 should be different for their easy identification. For example, conjugation is made with red LED 21, and accommodation follows with green LED 179.

Figure 6:
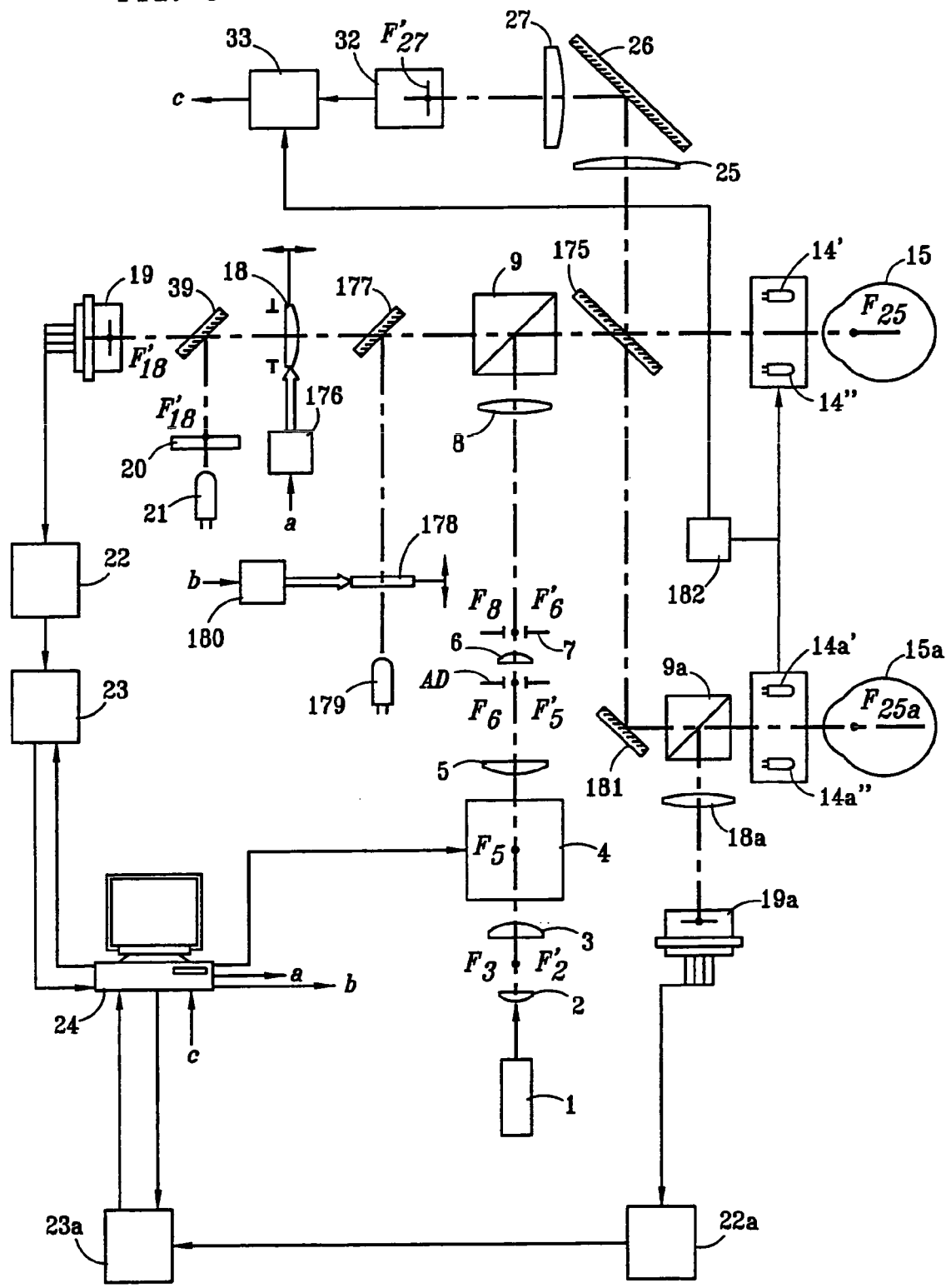
FIG. 6 is a schematic illustration of the operation of another embodiment of a device for measuring the total transverse aberration of a laser beam on the eye retina.

Still another embodiment of the invention, schematically shown in FIG. 6 and based generally on the configuration presented in the FIG. 5, enables simultaneous investigation of both eyes 15 and 15*a*. According to the design shown in FIG. 6 this embodiment beneficially contains an additional channel for the second eye 15*a*. The implementation is such that the common laser probing is used for both eyes due to two beam splitters 175 and 181. Optical and electrical components 9*a*, 14*a*, 18*a*, 19*a*, 22*a*, and 23*a* have the same roles as the corresponding components 9, 14, 18, 19, 22, and 23 at measurement of the first eye 15. Control unit 182 switches the infrared LEDs 14 and 14*a* to alternatively get irradiated first and second eye 15 and 15*a* respectively. In this way, images of the eyes can be displayed simultaneously, for example, on the left and right parts of the monitor's screen. Described implementation enables separate adjustment and advantageously provides simultaneous measurements on both eyes.

In the various embodiments of FIGS. 4, 5, and 6 the laser beam is positioned by the computer and the acousto-optic deflector so as to enter the pupil within the requisite refraction measurement zone. If the optical system of the eye has aberration refraction, the light image of the stop or diaphragm 7 on the retina is displaced from the axis, which results in the corresponding displacement of the illuminated zone image on the photosensitive surface of the position-sensing photodetector 19.

Figure 7:
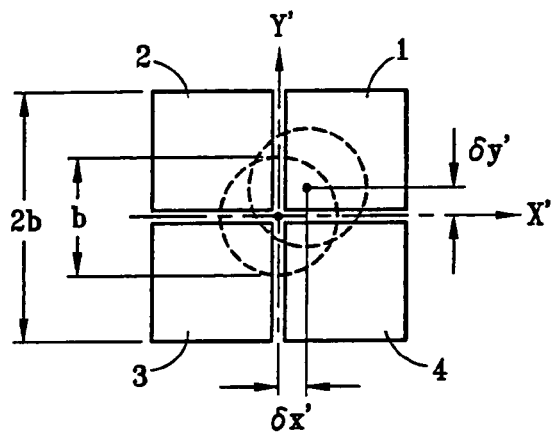
FIG. 7 is a schematic illustration of the operation of yet another embodiment of a device for measuring the total transverse aberration of a laser beam on the eye retina of both of a patient's eyes substantially simultaneously.

If photodetector 19 is a four-quadrant photodiode, as, for example, that shown digrammatically in FIG. 7, having quadrants 1, 2, 3 and 4, an aberration displacement of the light spot of δx, δy on the retina can be given by the formula:

$$\delta x = \frac{\beta}{2}\left[\frac{(U_1 + U_4) - (U_2 + U_3)}{U_1 + U_2 + U_3 + U_4}\right] \cdot b, \quad (1)$$

$$\delta y = \frac{\beta}{2}\left[\frac{(U_1 + U_2) - (U_3 + U_4)}{U_1 + U_2 + U_3 + U_4}\right] \cdot b, \quad (2)$$

where β is the transverse magnification in the plane of the first photodetector as related to the plane of the retina, b is a coefficient depending on the size of the light spot in the plane of the photodetector, and $U_1$, $U_2$, $U_3$ and $U_4$ are the photoelectric signals coming from the corresponding photodetector channels.

Figure 8:
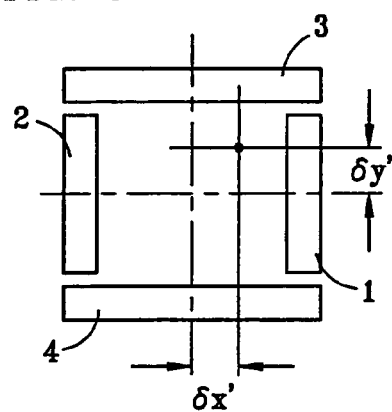
FIG. 8 is a schematic illustration of the operation of the lateral position sensing detector having a pair of X direction electrodes and a pair of Y direction electrodes.

If photodetector 19 is a lateral position sensing detector, as shown in FIG. 8, having a pair of x-direction electrodes 1 and 2, and a pair of Y-direction electrodes 3 and 4, an aberration displacement of the light spot δx, δy on the retina can be described as follows:

$$\delta x = \beta\left[\frac{U_1 - U_2}{U_1 + U_2}\right] \cdot a, \quad (3)$$

$$\delta y = \beta\left[\frac{U_3 - U_4}{U_3 + U_4}\right] \cdot a, \quad (4)$$

where β is the transverse magnification between the planes of photodetector and retina, $U_1$, $U_2$, $U_3$ and $U_4$ are the signals coming from the electrodes, 1, 2, 3 and 4 correspondingly, and a is a scaling coefficient depending on the electrical parameters of the lateral detector.

Figure 9:
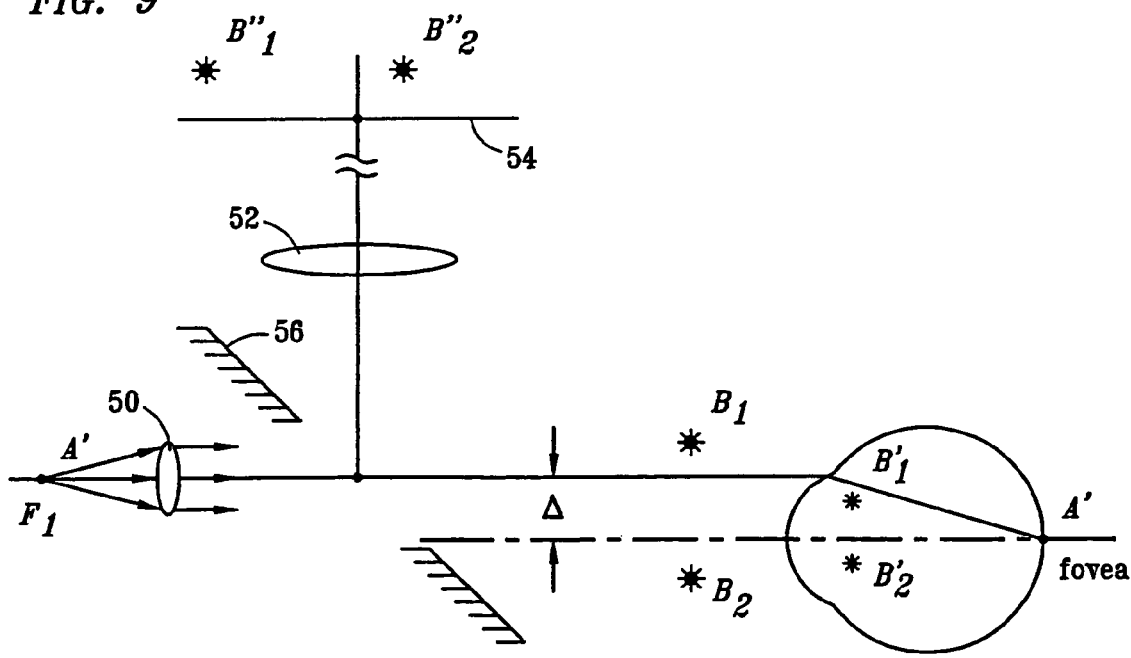
FIG. 9 is a schematic illustration of the principle of operation of the means for positioning the measuring device in relation to the patient's eye.

The principle of operation relating to the positioning the instrument in relation to the patient's eye is illustrated in FIG. 9. The collimating system 50 corresponds to the elements 39, 18 and 17, 16 of FIG. 4 (if the eye is accommodated at a finite distance). Point A is the light radiator and gaze fixation point and is formed by the elements 20 and 21 in FIG. 4. The mirror 56 with an opening corresponds to element 12 of FIG. 4. The microscope objective lens 52 is comprised of the elements 25-27 of FIG. 4 while the microscope objective image plane 54 (FIG. 4) corresponds to the element 29 (FIG. 4). $B_1$ and $B_2$ are light radiators corresponding to the LED 14 of FIG. 4. $B'_1$ and $B'_2$ are primary images of the radiators while $B''_1$ and $B''_2$ are secondary images of the radiators.

As can be seen from FIG. 9, the fixation of the gaze on the point A, located on the optical axis of the instrument, does not guarantee the coincidence or alignment of the visual axis of the eye and the optical axis of the instrument because the eye sees the point A on the fovea even when Δ≠0. The fixation of the gaze on the point A is ensured only when the above axes are parallel.

Taking into account that the largest contribution to the optical power of the eye is made by the anterior surface of the cornea, the visual axis line is assumed to be the line passing through the fovea center and the vertex of center of curvature of the front surface of the cornea. If the radiator $B_1$ is positioned in front of the patient's eye, then, due to reflection of the light from the anterior or front surface of the cornea, this surface functioning as a convex mirror, forms an imaginary or virtual image $B'_1$ of the radiator, located symmetrically to the axis in accordance with the laws of geometric optics.

When several radiators, such as for example, $B_1$ and $B_2$, are positioned in front of the patient's eye symmetrically to the optical axis of the instrument (FIG. 9), their secondary images $B''_1$ and $B''_2$ will be shifted in the image plane of the microscope objective lens aside from the axis if $\Delta \neq 0$.

Thus, to make the optical axis of the instrument and the visual axis of the eye coincide, two conditions must be satisfied: the patient's gaze is fixed on the point A and the images $B''_1$ and $B''_2$ are centrally positioned in relation to the axis of the objective lens 52. The positioning can be checked using the coordinate grid provided on the plate 29 (FIG. 1) or using the monitor screen when the TV channel is utilized. When the image of the eye is aligned at all points with concentric locations on the grid or the TV screen, the measurement controller is armed for taking a spatially resolved set of refraction measurements. The operator can than activate the measurement that can take only a few milliseconds. The measurements are "grabbed" in the grabber board and stored for producing an aberration refraction map as in FIG. 12. The measurements can also be activated automatically when the proper alignment is detected. Further, according to one embodiment of the invention, a plurality of measurements can be made sequentially during the occurrence of a predetermined event, such as through a sequence of movement of the eye target from a "near" accommodation distance to a "far" or infinity accommodation distance. A plurality of measurement images can be captured or automatically grabbed and stored over a time period or while any other changes are occurring for which eye measurements might indicate a dynamic change in the refraction of the eye.

The coincidence of the points $B''_1$ and $B''_2$ with the surface or plane 54 is indicative of setting the fixed working distance between the instrument and the eye which is the result of the focusing of the images $B''_1$ and $B''_2$ on the surface 54.

The point of gaze fixation is created by locating the mirror 39 (FIG. 4) on the optical axis of the instrument. The radiators 14' and 14" play the part of the radiators $B_1$ and $B_2$ shown in FIG. 9.

Another embodiment of eye instrument alignment can be implemented using manually or automatically operated measurement of the pupil edges; forming a figure, approximately a circle. Its center does not coincide usually with the center of symmetry of four reflexes, two of which $B''_1$ and $B''_2$ are shown in FIG. 9. This non-coincidence can be taken into consideration at further signal processing.

The calibration of the instant aberration refraction instrument may be effected using the optical calibration unit. The optical calibration unit can be made to incorporate known aberrations at the corresponding cornea simulator 34 measurement points. For example, the aberration may be determined by the computer using special optical design programs. If, for example, the front surface of the lens 34 is ellipsoidal, then the aberration refraction at all the points of the pupil is equal to zero.

When an ametropy compensator is used, nonparallel laser beams will enter the optical calibration unit. This will result in a standard aberration of defocusing; to compensate for this aberration, the retina simulator can be moved along the optical axis by means of the actuator 37 to the focus point. Thereby, the fovea can be optically conjugated with the retina simulator.

Systematic errors of measurements of the transverse aberration will be evidenced by the deviation of the measurement results from the estimated data. Such determinable systematic errors can be taken into account when measuring actual total ocular aberrations.

The calibration by comparison with the optical calibration unit is preferably performed automatically before measuring the ocular aberrations by locating the mirror 13 on the optical axis of the instrument.

Figure 10:
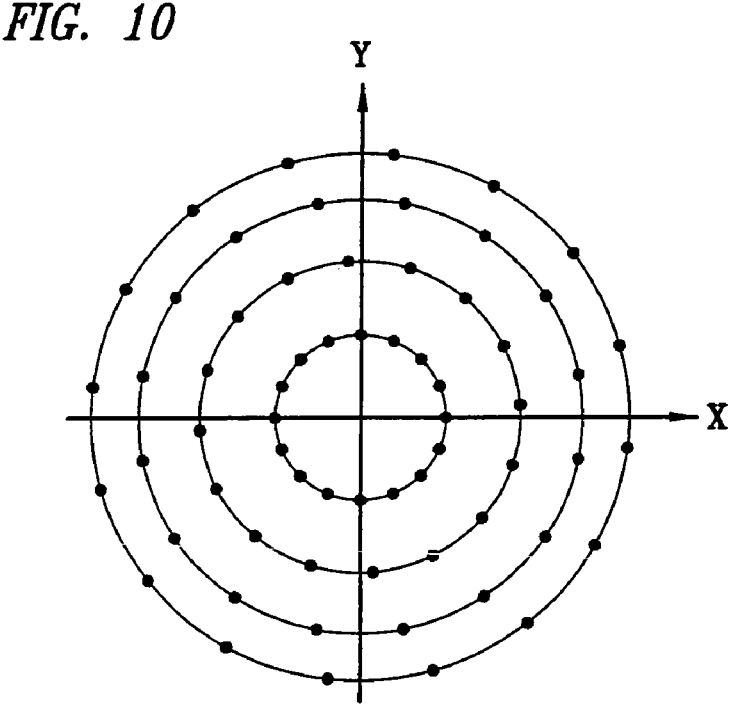
FIG. 10 is an example of a map showing the location of ocular refraction measurement points, constructed with the aid of a computer.

Prior to the ray tracing of the patient's eye the mirrors 13 and 39 are withdrawn from the light path entering the eye and then the light passes to the photodetector. The aberration displacement of the image of the light spot on the fovea is measured at a set of points on the cornea corresponding to an ocular ray tracing grid chosen by the operator. An example of a grid or an allocation of measurement points on the pupil is shown in FIG. 10.

The data on measurement of the transverse aberrations on the retina $\delta x\ (\rho, \phi)$ and $\delta y\ (\rho, \phi)$ are used for further calculations of the coefficients of the Zernike polynomials by means of the least squares method in order to approximate the function of the total wave aberration of the eye. The wave aberration function is then used to calculate the local total refraction at any point of the pupil. In addition, the approximation makes it possible to determine or reconstruct the nature of local aberration refraction in that small axial zone of the pupil, where it is impossible make accurate direct measurement of refraction.

In one experiment conducted using this instrument in which five replicate tests were performed and the results averaged, the laser beam total aberration on the retina at 65 points of the pupil was been performed in within 12 milliseconds with no more that 5 mW of light radiation entering the eye.

Figure 12:
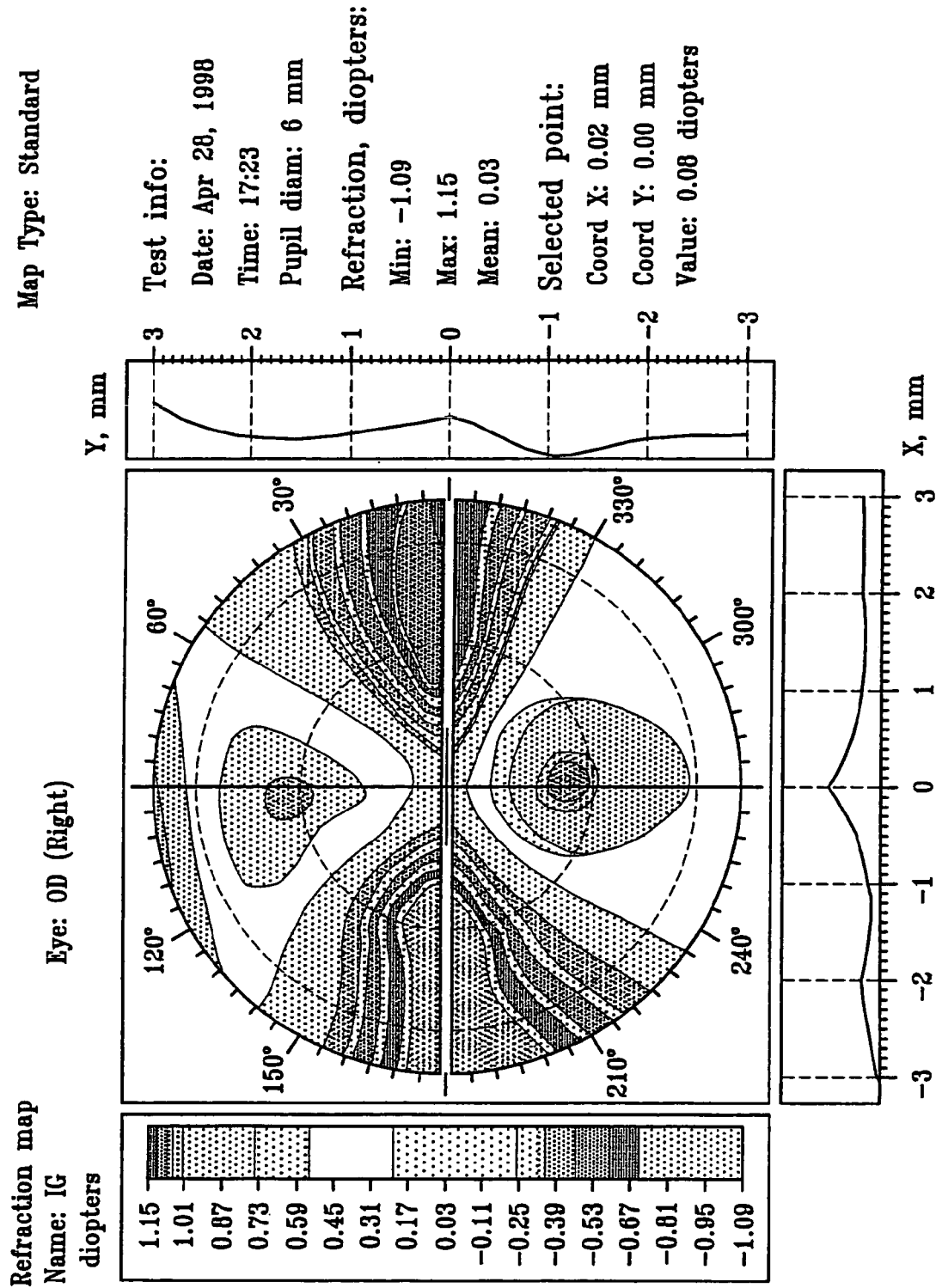
FIG. 12 is an example map showing the total aberration refraction of the eye, under consideration, constructed with the eye total aberration refractometer portion of the subject invention.

FIG. 12 is an example map showing the total aberration refraction of the eye, under consideration, constructed with the eye total aberration refractometer portion of the subject invention.

The extremely fast measurement permits the computer control program to cause a plurality of spatially resolved aberration measurements to be made in a very short period of time. The control program in one embodiment automatically activates a plurality of measurements coordinated with a series of adjusted accommodation fixation distances and automatic determination of proper eye alignment to receive a series of data measurements from the retinal spot position detecting channel. A series of refraction measurements for a dynamic eye refraction system is produced. Spatially resolved refraction measurements can be automatically programmed and automatically made during a variety of dynamic changes such as varying accommodation or during normal functioning of the eye under a variety of predetermined conditions and internal or external changing conditions.

It has been discovered by Applicants that combining techniques for analyzing total aberration refraction of the eye and for analyzing cornea shape and its refractive contribution, whether synchronously measured or sequentially measured within a period of time, provides useful information on the contribution of each component of the eye. It has also been discovered by Applicants that measuring or determining the total aberration refractive and the refractive components of the eye under varying conditions of accommodation (both near point and far focal points), varying conditions of pupil constriction(both dark and light conditions)to find the visual function of the eye at boundary conditions, at conditions in between the boundaries and visual function response to dynamically changing conditions may provide additional useful information on the total refraction and the contributions of each component of the eye. further the most natural and accurate measurements are taken with open field viewing by the patient and with binocular vision testing to avoid or reduce machine induced accommodation errors. Methods and devices for accomplishing these types of measurements and analyses have been variously disclosed in prior co-pending patent applications PCT/US02/12141; PCT/US02/24075; and PCT/US02/41853 all incorporated by reference herein. In particular it will be understood that non parallel rays of converging light, parallel rays, and diverging rays of light can be used to simulate various near and far vision conditions. Similarly, hollow lenses (either converging or diverging), or telescopic lenses, can be placed in front of the test eye to change the direction of parallel probing beams at the periphery of the pupil and thereby measure aspects of the eye function such as peripheral vision and night vision. Such information provides improved methods for correcting total refractive errors of the eye and/or errors associated with the intraocular lens rather than errors only of the cornea.

Although much of the foregoing description is directed to synchronous ray tracing for finding both the corneal topography and total refraction, it will be understood that other methods and devices for measuring total refraction and for measuring the corneal topography may also be used. The data can be coordinated or aligned for calculating the contributions of the cornea by locating and aligning the pupil center for each set of measurements whether synchronously taken or sequentially taken. Using the pupil center along with measurements of corneal limbal dimensions and apex location can be used to assist ultimate alignment and registration of the various measurements obtained. Iris pattern registration is possible as well for aligning or for confirming alignment of the data sets.

Figure 13:
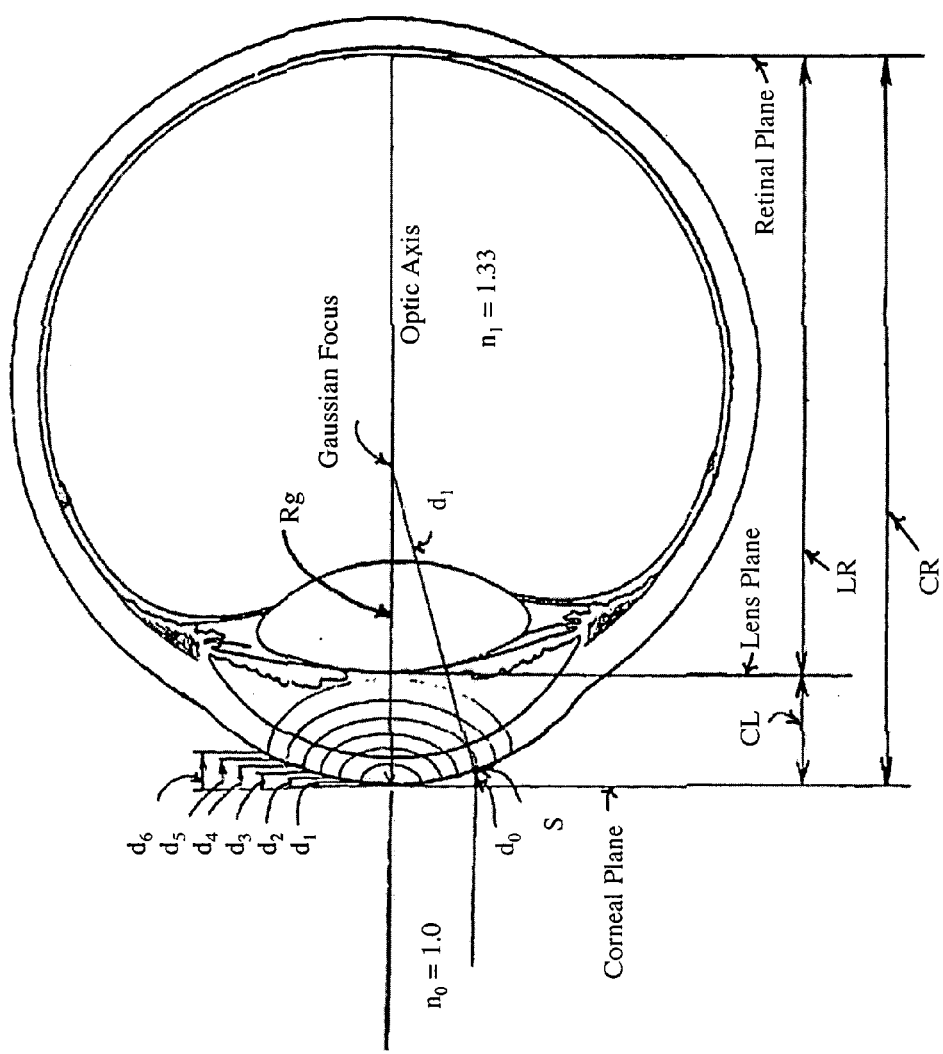
FIG. 13 is a schematic side cross-section of an eye demonstrating the different depth of the plane of the cornea compared to the depth of the plane of the intraocular lens plane and concentric ring pattern projection $d_1$ to $d_6$, and sagittal (S) depth measurement for determining of corneal topography.

For better understanding of the invention, reference is made to FIG. 13 showing an anatomical model of a human eye. It will be understood that the anterior plane or surface of the cornea (Corneal Plane) and the anterior plane or surface of the lens (Lens Plane) are offset by about 3.5 mm at (CL) measured along the optic axis. The index of refraction for air is $n(0)=1.0$, the index of refraction of the cornea and aqueous is $n(c)=1.337$ and $n(a)=1.337$, the index of refraction of the lens is $n(l)=1.420$ (the index of refraction of the lens typically varies slightly form the anterior surface to the posterior surface from about 1.386-1.406). The Optical Path Lenath Reference Sphere is modeled by $OPL_{REF}+Rg \times n_1$ and the Optical Path Length at Point S is modeled by $OPL_s=(d_0 \times n_0)+(d_1 \times n_1)$. Aberrations occurring at the cornea effectively act along the entire depth of the eye from the cornea to the retina (CL) and aberrations caused by the lens effectively act along the shorter distance from the lens to the retina (LR). Thus it can be seen that changing the shape of the cornea to correct for total aberration refraction can be inaccurate where the erroneous component of refraction is actually located at the lens.

The need for accommodation monitoring of the patient's eye has not been satisfied in prior art devices. As a consequence, the patient's eye can be accommodating at any distance during testing using prior devices and procedures. It is known that the refractive properties of the eye depend on the accommodation distance. Where the accommodation at which measurements are taken is unknown to the operator, it is impossible or at least very difficult to accurately correlate the refraction map and the eye accommodation. A device and method addressing natural accommodation have been disclosed in PCT/US02/24075 incorporated herein by reference.

It has become apparent to the present applicants that a spatially resolved refractometer should preferably include a device for adjusting to the patient's eye accommodation.

Systematic instrument errors have plagued prior aberration refractometers. Due to an irregular distribution of the light irradiance within the light spot on the retina, unequal photosensitivity across the surface photoelectric detector, time instability of the gain of preamplifiers connected to the photoelectric detector elements, and the presence of unsuppressed glares and background illumination the photodetector, the photodetector does not register a "zero" position of the spot on the fovea without systematic errors. Further, as a result of its own aberrations, the optical system providing for eye ray tracing contributes an angular aberration to the light beam position. Additionally, measurement under various conditions of pupil sizes (day light—small pupil size, to night time—large pupil size) and various accommodative states (near focal point—fully accommodated, to far focal point —fully relaxed) is beneficial for determining the boundaries of visual function for the eye under investigation and the range of visual function therebetween, as well as the dynamic response of the eye to changing conditions. The present inventive instrument and method incorporate structural elements and procedures which compensate for such errors and thus increase the refraction measurement accuracy.

Thus applicants provide an improved combination aberration refractometer with corneal topographical measuring device which makes it possible to achieve the following goals: ensuring optical coupling of the measurements of total aberration refraction to corneal topography to allow accurate determination of component contributions by the cornea and the lens or other aspects of the eye; accommodation monitoring at any given distance; measuring both the total eye refraction aberrations and the component caused by cornea refraction characteristics while maintaining incremental accuracy; reduction in instrument errors when measuring aberration refraction; enhancement of the accuracy and definitiveness of instrument positioning relative to the patient's eye; the potential for automation of the positioning and controllability of the working distance between the patient's eye and the device components; and enablement of instrument positioning without medically dilating the pupil. The present invention in its various alternative embodiments provides the aforementioned solutions and innovations.

Figure 14:
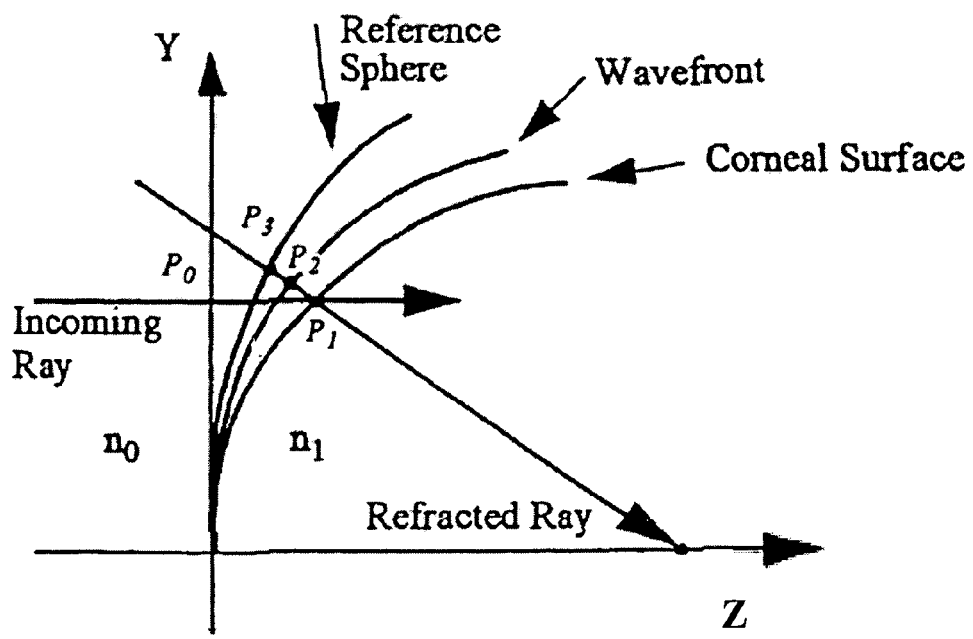
FIG. 14 is a schematic depiction of light rays and curved surfaces for wavefront aberration calculation.

The calculations required for determining wave front aberrations and then extracting the component contributed by the cornea may be better understood with reference for FIG. 14 in which one example for determining the corneal topography using placido rings is schematically depicted. A pattern of concentric rings are projected onto the cornea. Using the evenly spaced concentric rings the elevation or Sagitall Depth of points on each of the consecutive rings is derived with either Arc-step or spherical curve fitting.

Alternatively, the elevation can be measured by digital slit lamp stereography 3D or triangulation such as with an Orbscan device or a Pars Topo device.

It will be understood that the wavefront aberration of a ray at a point on the reference sphere where the ray intersects it, is defined as the difference between the optical path length (OPL) of the ray and the OPL of the chief ray. The wavefront aberration of an optical system for a given point object is determined by tracing rays from the object pint through the system and up to the Gaussian reference sphere, which is a spherical surface passing through the enter of the exit pupil and the center of the Gaussian image point.

Figure 15:
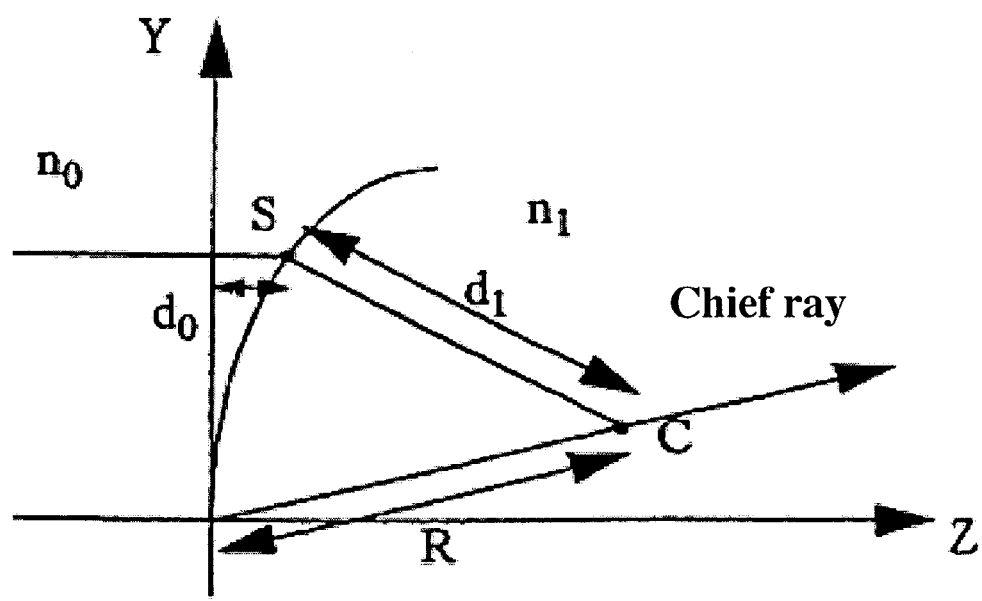
FIG. 15 is a schematic depiction of geometry for calculating the radius of the wavefront error reference sphere for calculating the difference of optical path length (OPL) of light passing through a point on the surface of the cornea to the Gaussian focal point, by which the component of refraction due to corneal topography may be calculated and then extracted (as by subtraction) from refraction measurements of the total eye.
Figure 16B:
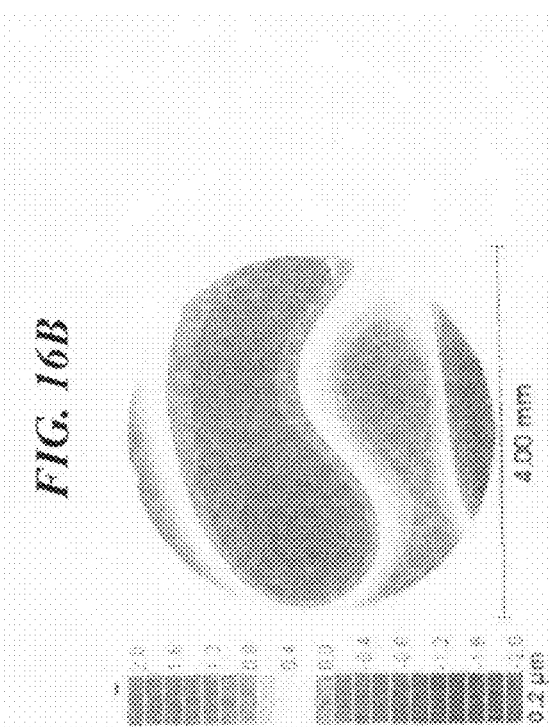
FIGS. 16A-16D are an example of a set of aberration refraction maps for an eye with vertical coma in the lens with a "with-the-rule" corneal astigmatism, showing component contributions to the total aberration refraction.
Figure 16A:
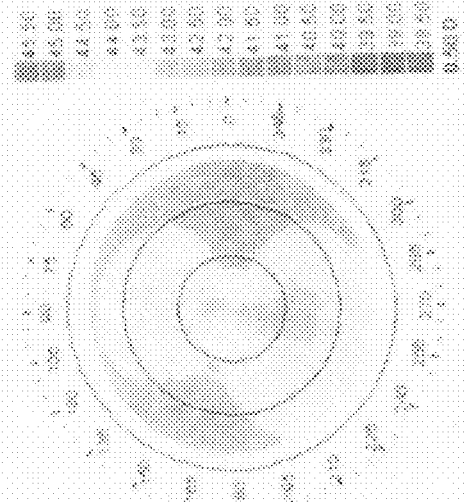
Figure 16D:
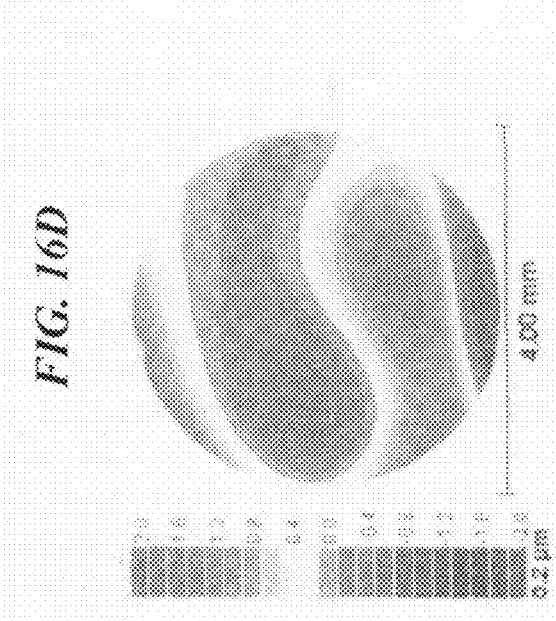
Figure 16C:
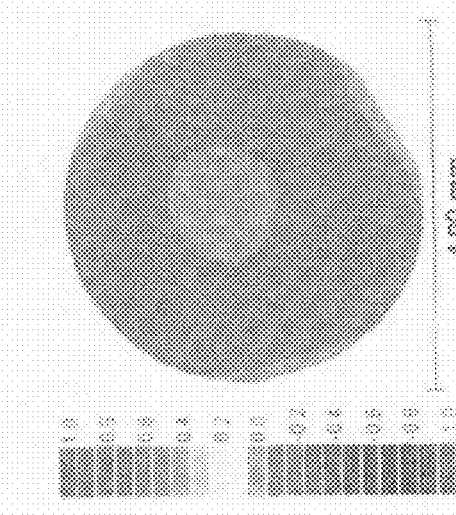

FIG. 15, shows the basic geometry for ray tracing analysis involved in the calculation of wave front aberration. An incoming ray intersects the exit pupil at point P0 and then intersects the corneal surface at P1. the ray is then refracted a at P1. the intersection of this refracted ray with the wavefront is at P2 and with the reference sphere at P3. the wave front, the reference sphere, and the corneal surface all pass through the origin as indicated in FIG. 16. Thus the optical path length from P0 to P1 to P2 must be zero as follows:

$$\|P_1-P_2\|+n_1\|P_1-P_2\|=0 \tag{5}$$

The procedure for finding the wavefront aberration for a given ray is:

1. Find the intersection point P1 of the incoming ray and the corneal surface.
2. Find the refracted ray direction at P1.
3 Find the wavefront intersection point P2 using Eq. (5) and the refracted ray direction from step 2.
4. Find the reference surface intersection point P3 using the refracted ray direction.
5. The wavefront aberration is the optical path length $\|n_1\|P_2-P_3\|$.

Generally, the magnitude of the wavefront aberration will correspond to the differences between the measured optical path length, of a light ray passing through a given point on the cornea, and the optical path length through the same location on a model cornea providing ideal optical focus. Thus, the wave front aberration may be considered as measured in terms of the optical path length.

From the measured topography of the cornea a reference curve (sphere) is derived for anterior cornea at the pupil center point coincident with the optical axis. The calculation of the wavefront error reference sphere employs the geometry illustrated in FIGS. 16A-16D. The reference sphere has its front vertex at the origin so that there is no distance between the refracting surface and the reference sphere. Thus, calculations are made to find the center of the reference sphere. For perfect focus, at each intersection point S the optical path length of S.sub.z.times.n.sub.0+.vertline.C-S.vertline..times.n.sub.1 is equal to the reference radius R.times.n.sub.1 as indicated in (6).

$$d_0 \times n_0 + d_1 \times n_1 = R \times n_1 \tag{6}$$

The location of the reference sphere center C is a function of the chief ray direction vector as shown in (7).

$$\begin{bmatrix} x_c \\ y_c \\ z_c \end{bmatrix} = R \begin{bmatrix} x_d \\ y_d \\ z_d \end{bmatrix} \tag{7}$$

In the following the norm of the direction vector has unit length. Expanding (6) and applying (7) gives the condition for perfect focus as in (8).

$$z_s \times n_0 + [(x_s-Rx_d)^2+(y_s-Ry_d)^2+(z_s-Rz_d)^2]^{1/2} \times n_1 = R \times n_1 \tag{8}$$

Solve (8) for R as shown in (9), setting the index of refraction for air at $n_0=1.0$.

$$R = \frac{S^T S - \frac{z_s^2}{n_1^2}}{2\left(\frac{z_s}{n_1} - S^T D\right)} \tag{9}$$

Apply (9) and (7) to a dense sampling of the surface, identifies a set of reference sphere centers for the surface. This calculation is performed for all data points in the original corneal topography exam.

FIGS. 16A-16D are an exemplary set of aberration refraction maps for an eye with vertical coma in the lens with a "with-the-rule" corneal astigmatism, showing component contributions to the total aberration refraction. These figures are derived from a method for measuring the aberration refraction of the components of the eye, includes measuring the total aberration refractive characteristics of the eye measuring the corneal shape of the eye and therefore its refractive power, calculating the aberrations of the cornea from the refractive power, calculating the difference between the values of the total aberration refractive characteristics of the total eye and the cornea, storing refractive characteristics measured and calculated above, transforming the refractive characteristics of the components into continuous three-dimensional distributions of the refractive characteristics and displaying the three dimensional distributions of the refractive characteristics.

The total aberration refraction of the eye and the corneal shape of said eye and its associated refractive power are measured either synchronously or sequentially.

The total aberration refraction of the eye can be measured using ray tracing to determine the refractive characteristics of each eye at a plurality of spatially resolved locations on the eye and an estimated expression of the refraction characteristics base upon best fit by a curve fitting algorithm is calculated from the plurality of refractive characteristics at the plurality of spatially resolved locations. In one embodiment the curve-fitting algorithm is a Zernike polynomial expansion. In another embodiment the curve-fitting algorithm comprises a polynomial expansion series.

In yet another embodiment the curve-fitting algorithm is a spline mathematical calculation. Patent application PCT/US03/31610 shows such curve fitting a method and is incorporated by reference herein.

In one embodiment the total aberration refraction of the eye is measured using Hartman-Shack wavefront sensing to determine the refractive characteristics of each eye. An expression of refraction based upon best fit to a curve fitting mathematical function is calculated from the Hartmann-Shack wavefront analysis.

In one embodiment the total aberration refraction of the eye is measured using an aberroscope to determine distortion in a grid projected on the eye to indicate the refractive characteristics of the eye. An estimated expression of refraction based upon best fit to a mathematical function is calculated from the aberroscope grid distortions.

In one embodiment the total aberration refraction of the eye is measured using a device based upon the Foucault's knife sciascopy measurement method [5] to measure the refractive characteristics of the eye. An estimated expression of refraction based upon best fit to a mathematical function is calculated from the sciascopy measurement.

In one embodiment measuring the corneal shape of the eye and its associated refractive power is accomplished by projecting a regular structure or regular patterns, such as a pattern of concentric rings onto the cornea. The reflected light data is analyzed and the shape of the cornea is reconstructed from the analyzed light data indicative of the refraction distribution caused by the cornea. The refractive power is analyzed by means of a best-fit mathematical function to calculate the aberrations of the cornea. For example the regular pattern is one consisting of alternating light and dark spots on concentric rings to form what appears similar to a checkerboard pattern.

In one embodiment the corneal shape of the eye and its associated refractive power is measured using a laser ray tracing technique wherein a plurality of sequential thin beams impinge the cornea of the eye at a plurality of locations causing a portion of the beam to be reflected from the corneal surface. A position-sensitive detector is used to determine the angle of the reflected beams. Calculations are made based upon the angles of incident of the reflected beams at different points to determine the corneal shape and refractive power. Further calculations are made to determine the aberrations of the corneal surface. An example of a device and method for calculations made based upon the angles is disclosed in PCT/US02/41853 incorporated herein by reference.

In one example, the plurality of thin ray tracing light beams are polarized light, such as either laser light or other high intensity polarized light. In another example, the plurality of thin ray tracing light beams non-polarized, such as light produced by super luminescent radiant diodes.

Referring again to FIGS. 16A-16D, the lower right hand corner, FIG. 16A, shows a corneal topography map derived from measurements that may be obtained with ray tracing or with standard concentric ring pattern projection or checkerboard pattern projection and sagittal depth measuring techniques using devices such as are available from EyeSys. Here a corneal topography map is shown demonstrating with-the-rule astigmatism. The upper right hand corner, FIG. 16B, demonstrates a wavefront map of the total higher order aberrations in the same eye from a ray tracing measurement as with a Tracey Technologies instrument. Vertical coma is clearly seen as the dominant higher order aberration in this eye. By performing Zernike analysis on the corneal topography map the higher order aberrations generated exclusively by the cornea can be calculated and is shown in the lower left hand corner map, FIG. 16C. In this case, it clearly shows a typical pattern of spherical aberration. By "subtracting" this map from the higher order aberration map of the total eye measured by the Tracey instrument, a wavefront map of the higher order aberrations generated by the lens is produced as shown in the upper left hand corner, FIG. 16D. This result clearly reveals that the source of the vertical coma in the eye is primarily from the lens.

Figure 17A:
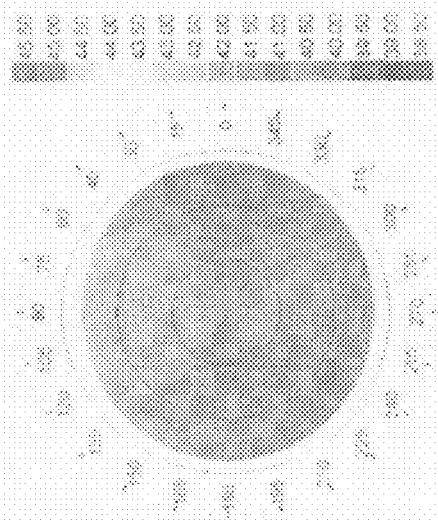
FIGS. 17A-17D are an example of a set of aberration refraction maps for an eye with horizontal coma in the lens with a spherical cornea, showing component contributions to the total aberration refraction.
Figure 17B:
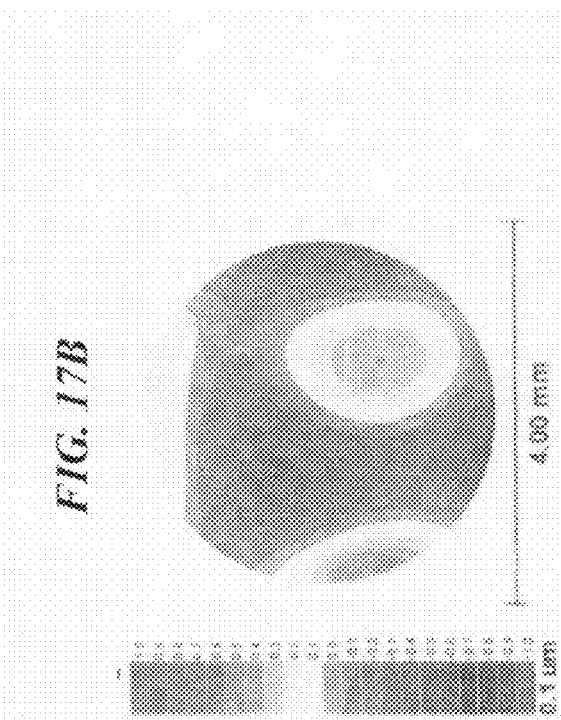
Figure 17C:
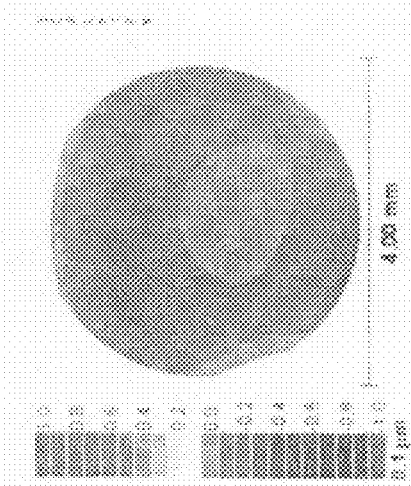
Figure 17D:
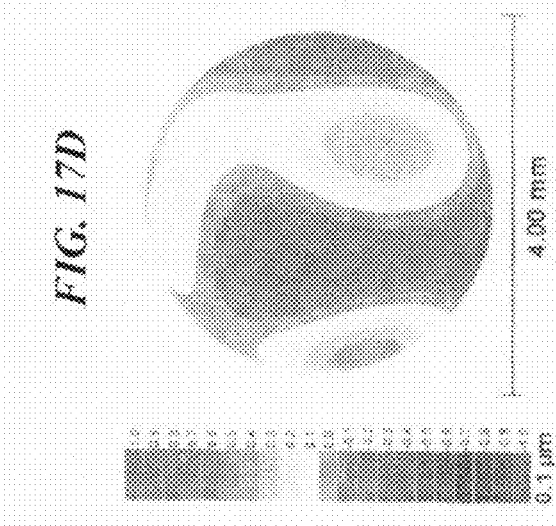

FIGS. 17A-17D are an exemplary set of aberration refraction maps for an eye with horizontal coma in the lens with a spherical cornea, showing component contributions to the total aberration refraction. The lower right hand corner, FIG. 17A, shows a standard projected rings corneal topography map demonstrating a normal spherical cornea. The upper right hand corner, FIG. 17B is a wavefront map of the total higher order aberrations in the same eye from a Tracey measurement. Horizontal coma with a little trefoil are seen as the major higher order aberrations in this eye. By performing Zernike analysis on the corneal topography map the higher order aberrations generated by the cornea which are shown to be mostly spherical aberration, FIG. 17C. By subtracting this map from the higher order aberration map of the total eye measured by the Tracey a wavefront map of the higher order aberrations of the lens is produced. This map in the upper left hand corner, FIG. 17D reveals that the source of the horizontal coma and trefoil in this eye is primarily the lens.

Figure 18A:
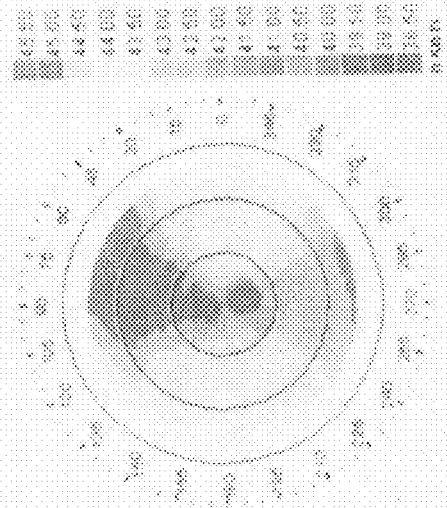
FIGS. 18A-18D are an example of a set of aberration refraction maps for an eye with asymmetric astigmatism that causes high order corneal aberrations, showing component contributions to the total aberration refraction.
Figure 18B:
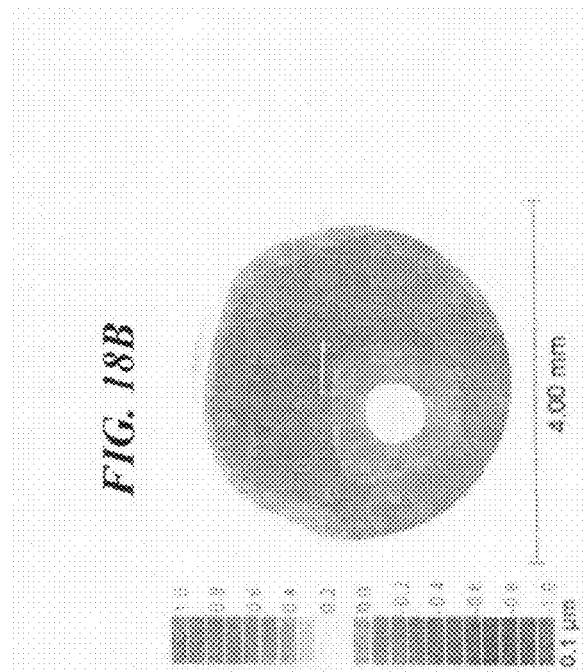
Figure 18C:
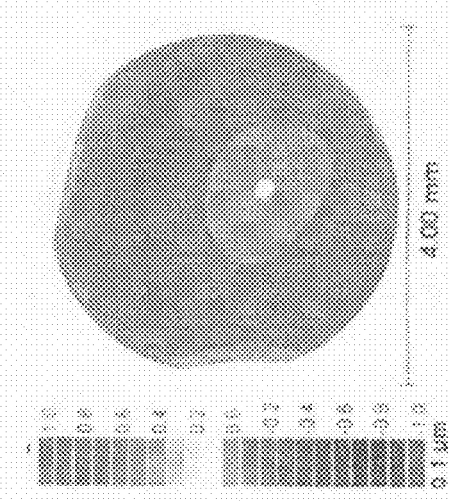
Figure 18D:
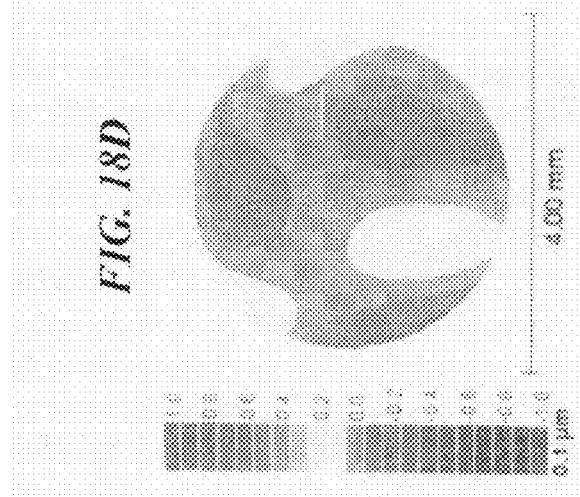

FIGS. 18A-18D are an exemplary set of aberration refraction maps for an eye with asymmetric astigmatism that causes higher order (H-O) corneal aberrations, showing component contributions to the total aberration refraction. The lower right hand corner, FIG. 18A, shows a standard projected rings (EyeSys) corneal topography map demonstrating asymmetric astigmatism which is common with a displaced corneal apex. The upper right hand corner, FIG. 18B, demonstrates a wavefront map of the total higher order aberrations in the same eye from a Tracey measurement. Spherical aberration and some vertical coma are seen as the major higher order aberrations in this eye. By performing Zernike analysis on the corneal topography map the higher order aberrations generated by the cornea can be calculated, FIG. 18C. This analysis shows a similar pattern of spherical aberration and vertical coma as in the Tracey total higher order aberration map in the upper right, FIG. 18B. The higher order aberrations of the lens in the upper left, FIG. 18D, show a mostly green map indicating little higher order aberrations. Therefore, the higher order aberrations of the entire eye are generated primarily by the cornea. This eye would is ideally suited for custom-driven LASIK.

Because of the offset between the plane of the cornea and the plane of the lens (see FIG. 13) the amount of custom LASIK ablation at each point on the cornea is adjusted, or the form of the lens is adjusted, to compensate for the difference that results from the relative offset positions of the cornea and the lens. Thus, by knowing which portion or the aberration is actually caused by which component of the eye corrections applied either at the cornea or at the lens can be made to more accurately provide vision correction.

In one embodiment where custom correction is intended to be accomplished only by corneal ablation, the an eye is computer program modeled having the measured component of refraction at the cornea and the measured component of refraction at the lens. A computer program is used to employ appropriate know algorithms in a computer program to simulate a ray tracing analysis of the modeled eye. The cornea of the modeled eye is modified in the computer program according to LASIC application vision correction algorithms. The model eye thus modified at the cornea and together with the lens with the forgoing measured aberrations is again subjected to a computer simulated ray tracing analysis. Because of the lens aberration the original corrections to cornea will demonstrate uncorrected error. The cornea is then computer modified again to further correct the lens caused error. With the high speed of modern computers, th simulation can be iteratively conducted numerous times until the residual aberrations are sufficiently diminished. The total resulting total correction to the cornea may then be applied in an actual surgery to the patient's cornea for optimized vision correction. It will be understood that where, for example, the major component of aberration is found in the lens, the same technique of iterative computer modeling of successive corrections to the lens can provide optimal correction with appropriately formed intraocular lens replacement without corneal ablation. In another embodiment both corneal ablation of the corneal aberration component and intraocular lens replacement to correct the lens component of aberration can also optimize vision correction Those skilled in the art will understand that additional features of the invention are obtained by combining the teachings herein with those set forth in co-pending co-owned patent application PCT/US02/12141, incorporated by reference herein. According to one alternative embodiment, measuring the total eye aberration refraction may include making measurements at continuously varying states of patient eye accommodation.

According another alternative embodiment measuring the total eye aberration refraction may include making measurements at fixed intervals of accommodation.

According another alternative embodiment measuring the total eye aberration refraction may include making the measurements under continuously varying lighting conditions from scotopic to photopic.

According another alternative embodiment measuring the total eye aberration refraction may include making the measurements at predetermined intervals of light illumination to simulate scotopic, mesoptic and photopic conditions.

The total aberration refraction of the eye can be measured using ray tracing to determine the refractive characteristics of each eye at a plurality of spatially resolved locations on the eye and an estimated expression of the refraction characteristics base upon best fit by a curve fitting algorithm is calculated from the plurality of refractive characteristics at the plurality of spatially resolved locations Thin beams are used for the ray tracing in which a plurality of thin beams are impinged upon the corneal surface parallel to each other to simulate a far point light source. Another plurality of thin beams are impinged upon the corneal surface non-parallel to each other to simulate a near point light source. This may for example be accomplished using a lens with hole in middle, placed in front of the eye to create diverging or converging beams of light into eye (other angles besides just parallel) to simulate rays from a near point target diverging onto the cornea. This may also simulate peripheral vision or skew beams into the eye. This can also be achieved with a moving telescope optical system or by using a mirror system around the periphery of the device.

It has been discovered that an analysis of the aberration refractive characteristics of the components of the eye determined are useful to improve the outcome of corneal refractive surgery. In particular, if the major portion of astigmatic and/or higher order aberrations of the total eye are on the corneal surface, then refractive surgery to provide of the cornea will provide optimal results. If a significant fraction of astigmatic and/or higher order aberrations of the total eye are on the internal optics (non-corneal), then the outcome of refractive surgery will not provide optimal results without other corrective actions also being taken. Current standards can be used by generating a wavefront error 3D map and building a tissue removal program off of the cornea surface to ablate enough tissue on a micron by micron basis to fit the wavefront error map according to the characteristic patterns generated by a specific laser. Corneal surgery might not be indicated or not recommended in the second situation.

It has been discovered that an analysis of the aberration refractive characteristics of the components of the eye determined are useful to improve the outcome of intraocular lens (IOL) replacement surgery. In particular, if the major portion of astigmatic and/or higher order aberrations of the total eye are on the corneal surface, then surgery to replace the intraocular lens with a standard IOL will be optimized. If a significant fraction of astigmatic and/or higher order aberrations of the total eye are on the internal optics (non-corneal), then the outcome of surgery to replace the intraocular lens with a standard IOL is not optimized.

Thus, customized corrective actions such as custom lasik surgery, according to one aspect of the inventions, involves full knowledge of aberration sources such as lens or corneal. Since the laser correction occurs on the cornea it will only change this plane of optics in the eye. If, for example, the lens is the source of a significant aberration, such as coma, which occurs quite frequently then a simple transference of that aberration to the cornea to correct it is insufficient. By modeling the eye and using even standard eye models as to the anterior chamber depth or including such data directly from measurement as with A-Scan ultrasound, then modifications to the custom ablation can account for the optical differences created with the source of aberration being on the lens. Appropriate aspheric changes and location of the center of refractive correction with regards to the pupil and lens can provide a significant improvement to the patient's overall vision satisfaction. Compromises between simple correction for far vision only versus alterations for maintaining good quality of peripheral vision or for near vision as may be most appropriate for the patient. Through dynamic refraction measurement testing all conditions of the eye's refractive state between near and far and night and day this information can be fully utilized. With binocular open field testing in addition, avoidance of instrument accommodation which is common with all current systems can be avoided and used to obtain a better baseline refraction for each patient to help maximize their accommodative range and preserve their reading vision as long as possible.

It has been discovered that analysis of the aberration refractive characteristics of the components leads to new algorithms for refractive surgery to allow for various optimal corrective measures as follows:

optimized correction based on near and far point data, optimized correction based on an analysis of various states of eye accommodation, and optimized correction based on an analysis of various states of pupil constriction.

Modeling and Ray Tracing techniques of the eye can be used to refine these improved custom algorithms from corneal topography data and wavefront/aberrometry data. A clinical protocol that maps out the patient's true far point refraction through binocular open field testing and then combines that with traditional fogging techniques to assess resting accommodative states and then by measuring at a maximized near point target to measure accommodative range of the patient will provide better data to set the target results for custom correction and preserve visual performance in all conditions. This approach will also include consideration of pupil characteristics as to size and centration under all conditions from scotopic to photopic and with accommodative miosis.

It has further been discovered that analysis of the aberration refractive characteristics of the components of the eye leads to the manufacture of custom intraocular lens that correct existing aberrations of the internal optics of an eye.

REFERENCES

1. M. S. Smirnov. Measurement of wave aberration of the eye. Biofizika (Biophysics USSR), 6, pp. 776-794,1961.
2. Van den Brink. Measurement of the geometrical aberrations of the eye. Vision Res. 2, pp. 233-244,1962.
3. N. M. Sergienko. Oftalmologicheskaya optika (Ophtalmic Optics). Moscow, Meditsina, 1991, 142 pages.

4. R. H. Webb, C. M. Penney, and K. D. Thompson. Measurement of ocular local wavefront distortion with a spatially resolved refractometer. Applied Optics. 31, pp. 3678-3686, 1992.
5. S. G. El Hage and Bemi F. Contribution of the crystalline lens to the spherical aberration of the eye. J. Opt. Soc. Am. 63, pp. 205-211,1973.
6. J. Liang. A new method to precisely measure the wave aberrations of the human eye with a Hartmann-Shack wave-front sensor, Ph. D. Dissertation, University of Heidelberg, Heidelberg, Germany, 1991.
7. J. Liang, B. Grimm, S. Goelz, and J. F. Bille, Objective measurement of wave aberrations of the human eye with the use of a Hartmann-Shack wave-front sensor. J Opt. Soc. Am. A 11, pp. 1949-1957,1994.
8. J. Liang and D. R. Williams. Aberrations and retinal image quality of the normal human eye. J Opt. Soc. Am. A 14, pp. 2873-2883, 1997.
9. J. Liang, D. R. Williams, and D. T. Miller. Supernormal vision and high resolution retinal imaging through adaptive optics, J. Opt. Soc. Am., A 14, pp. 2884-2892, 1997.
10. U.S. Pat. No. 5,258,791. Spatially resolved objective autorefractometer, Nov. 2, 1993.
11. T. Seiler, P. J. McDonnell, "Excimer laser photorefractive keratectomy", Surv. of Ophthalm., 40, pp. 89-118, 1995.

While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A method for measuring the aberration refraction of the components of the eye, said method comprising:
   a) measuring the total aberration refractive characteristics of said eye;
   b) measuring the corneal shape of said eye and therefore its refractive power;
   c) calculating the aberrations of said cornea from the refractive power;
   d) calculating the difference between the values of said total aberration refractive characteristics of the total eye and the cornea;
   e) storing refractive characteristics measured and calculated by 1(a), 1(b), 1(c) and 1(d) hereof;
   f) transforming the refractive characteristics of said components into continuous three-dimensional distributions of said characteristics; and
   g) displaying said three dimensional distributions of said refractive characteristics.

2. The method recited in claim 1 wherein the steps of measuring the total aberration refraction of said eye 1(a) and measuring the corneal shape of said eye and its associated refractive power 1(b) are measured either synchronously or sequentially.

3. The method recited in claim 1 wherein the step of measuring the total aberration refraction of said eye comprise the steps of:
   a) using ray tracing to determine the refractive characteristics of each eye at a plurality of spatially resolved locations on the eye; and
   b) calculating from the plurality of refractive characteristics at the plurality of spatially resolved locations an estimated expression of the refraction characteristics base upon best fit by a curve fitting algorithm.

4. The method of claim 3 wherein the curve-fitting algorithm comprises a Zernike polynomial expansion.

5. The method of claim 3 wherein the curve-fitting algorithm comprises a polynomial expansion series.

6. The method of claim 3 wherein the curve-fitting algorithm comprises spline mathematical calculations.

7. The method of claim 1 wherein the step of measuring the total aberration refraction of said eye comprises the steps of:
   a) using Hartman-Shack wavefront sensing to determine the refractive characteristics of each eye; and
   b) calculating from the Hartmann-Shack wavefront analysis an expression of refraction based upon best fit to a curve fitting mathematical function.

8. The method of claim 1 wherein the step of measuring the total aberration refraction of said eye comprises the steps of:
   a) using an aberroscope to determine distortion in a grid projected on the eye to indicate the refractive characteristics of said eye; and
   b) calculating from the aberroscope grid distortions an estimated expression of refraction based upon best fit to a mathematical function.

9. The method of claim 1 wherein the step of measuring the total aberration refraction of said eye comprises the steps of:
   a) using a device based upon the Foucault's knife method [5] to measure the refractive characteristics of said eye; and
   b) calculating from sciascopy measurement an estimated expression of refraction based upon best fit to a mathematical function.

10. The method of claim 1 wherein the step of measuring the corneal shape of said eye and its associated refractive power comprises the step of;
    a) projecting a regular structure or regular patterns, such as a pattern of concentric rings onto the cornea; and
    b) analyzing the reflected light and reconstruction from the analyzed data the shape and therefore the refraction distribution caused by the cornea; and
    c) analyzing said refractive power by means of a best-fit mathematical function to calculate the aberrations of said cornea.

11. The method of claim 10 wherein said regular pattern consist of alternating light and dark spots on said concentric rings (checkerboard pattern).

12. The method of claim 1 wherein the step of measuring the corneal shape of said eye and its associated refractive power comprises the steps of:
    a) using a laser ray tracing technique wherein a plurality of sequential thin beams impinge the cornea of the eye at a plurality of locations causing a portion of the beam to be reflected from the corneal surface; and
    b) using a position-sensitive detector to determine angle of the reflected beams;
    c) performing calculations to determine the corneal shape and refractive power; and
    d) performing calculations to determine the aberrations of the corneal surface.

13. The method of claim 12 wherein the said plurality of thin ray tracing beams are polarized.

14. The method of claim 12 wherein the said plurality of thin ray tracing beams are non-polarized.

15. The method of claim 1 wherein the step of measuring the total eye aberration refraction comprises making the measurements at continuously varying states of patient accommodation.

16. The method of claim 1 wherein the step of measuring the total eye aberration refraction comprises making the measurements at fixed intervals of accommodation.

17. The method of claim 1 wherein the step of measuring the total eye aberration refraction comprises making the measurements under continuously varying lighting conditions from scotopic to photopic.

18. The method of claim 1 wherein the step of measuring the total eye aberration refraction comprises making the measurements at fixed intervals of light illumination to simulate scotopic, mesoptic and photopic conditions.

19. The method of claim 3 wherein the thin beams for the ray tracing method of determining the total aberration refraction of the eye comprises the steps;
 a) plurality of thin beams impinge upon the corneal surface parallel to each other (far point light source); and
 b) plurality of thin beams impinge upon the corneal surface non-parallel to each other (near point light source).

20. A method as in claim 1 whereby analysis of the aberration refractive characteristics of the components of the eye determined in 1(d) is used to improve the outcome of corneal refractive surgery by the steps of;
 a) if the major portion of astigmatic and/or higher order aberrations of the total eye are on the corneal surface, then recomending refractive surgery; and
 b) if a significant fraction of astigmatic and/or higher order aberrations of the total eye are on the internal optics (non-corneal), then not recommending refractive surgery.

21. A method as in claim 1 whereby analysis of the aberration refractive characteristics of the components of the eye determined in 1(d) is used to improve the outcome of intraocular lens replacement surgery by the steps of:
 a) if the major portion of astigmatic and/or higher order aberrations of the total eye are on the corneal surface, then recommending surgery to replace the intraocular lens with a standard IOL; and
 b) if a significant fraction of astigmatic and/or higher order aberrations of the total eye are on the internal optics (non-corneal), then not recommending the surgery to replace the intraocular lens with a standard IOL.

22. A method as in claim 19 further comprising formulating new algorithms for refractive surgery by analysis of the aberration refractive characteristics of the components of the eye determined in 1(d) to obtain optimized correction based on boundaries of visual function for near and far point data.

23. A method as in claim 16 further comprising formulating new algorithms for refractive surgery by analysis of the aberration refractive characteristics of the components of the eye determined in 1(d) to obtain optimized correction based on an analysis of various states of eye accommodation.

24. A method as in claim 18 further comprising formulating new algorithms for refractive surgery by analysis of the aberration refractive characteristics of the components of the eye determined in 1(d) to obtain optimized correction based on an analysis of various states of pupil constriction.

25. A method of claim 1 further comprising analyzing the aberration refractive characteristics of the components of the eye determined in 1(d) and manufacturing a custom intraocular lens that corrects existing aberrations of the internal optics of an eye.

26. An instrument for measuring the aberration refraction of the components of the eye, said instrument comprising:
 a) means for measuring the total aberration refractive characteristics of said eye; and
 b) means for measuring the corneal shape of said eye and therefore its refractive power; and
 c) means for calculating the aberrations of said cornea from the refractive power; and
 d) means for calculating the difference between the values of said total aberration refractive characteristics of the total eye and the cornea; and
 e) means for storing refractive characteristics calculated by means of 26(a), 26(b), 26(c) and 26(d); and
 f) means for transforming the refractive characteristics of said components into continuous three-dimensional distributions of said characteristics; and
 g) means for displaying said three dimensional distributions of said refractive characteristics.

27. The instrument recited in claim 26 wherein the means for measuring the total aberration refraction of said eye 26(a) and the means for measuring the corneal shape of said eye and its associated refractive power 26(b) are coupled for either synchronously measuring the shapes or sequentially measuring the shapes.

28. The instrument of claim 26 wherein the means for measuring the total aberration refraction of said eye comprise:
 a) a ray tracing device used to determine the refractive characteristics of each eye at a plurality of spatially resolved locations on the eye; and
 b) a means for calculating from the plurality of refractive characteristics at the plurality of points an estimated expression of the refraction characteristics base upon best fit by a curve fitting algorithm.

29. The instrument of claim 28 wherein the curve-fitting algorithm comprises a Zernike polynomial expansion.

30. The instrument of claim 28 wherein the curve-fitting algorithm comprises a polynomial expansion series.

31. The instrument of claim 28 wherein the curve-fitting algorithm comprises spline mathematical calculations.

32. The instrument of claim 26 wherein the step of measuring the total aberration refraction of said eye comprises the steps of:
 a) using Hartman-Shack wavefront sensing to determine the refractive characteristics of each eye; and
 b) calculating from the Hartmann-Shack wavefront analysis an expression of refraction based upon best fit to a curve fitting mathematical function.

33. The instrument of claim 26 wherein the step of measuring the total aberration refraction of said eye comprises the steps of:
 a) using an aberroscope to determine distortion in a grid projected on the eye to indicate the refractive characteristics of said eye; and
 b) calculating from the aberroscope grid distortions an estimated expression of refraction based upon best fit to a mathematical function.

34. The instrument of claim 26 wherein the step of measuring the total aberration refraction of said eye comprises the steps of:

a) using a device based upon the Foucault's knife method [5] to measure the refractive characteristics of said eye; and b) calculating from sciascopy measurement an estimated expression of refraction based upon best fit to a mathematical function.

35. The instrument of claim 26 wherein the step of measuring the corneal shape of said eye and its associated refractive power comprises the step of;

a) projecting a regular structure or regular patterns, such as a pattern of concentric rings onto the cornea; and b) analyzing the reflected light and reconstruction from the analyzed data the shape and therefore the refraction distribution caused by the cornea; and c) analyzing said refractive power by means of a best-fit mathematical function to calculate the aberrations of said cornea.

36. The instrument of claim 33 wherein said regular pattern consist of alternating light and dark spots on said concentric rings (checkerboard pattern).

37. The instrument of claim 26 wherein the step of measuring the corneal shape of said eye and its associated refractive power comprises the steps of:

a) a laser ray tracing technique wherein a plurality of sequential thin beams impinge the cornea of the eye at a plurality of locations causing a portion of the beam to be reflected from the corneal surface; and b) a position-sensitive detector determines to angle of the reflected beams; and c) calculations are preformed to determine the corneal shape and refractive power; and d) calculations are preformed to determine the aberrations of the corneal surface.

38. The instrument of claim 37 wherein the said plurality of thin ray tracing beams are polarized.

39. The instrument of claim 37 wherein the said plurality of thin ray tracing beams are non-polarized.

40. The instrument of claim 28 wherein the said ray tracing uses polarized light beams.

41. The instrument of claim 28 wherein the said ray tracing uses non-polarized light beams.

42. The instrument of claim 26 further comprising means for measuring the total eye aberration refraction at continuously varying states of patient accommodation.

43. The instrument of claim 26 further comprising means for measuring the total eye aberration refraction at fixed intervals of accommodation.

44. The instrument of claim 26 further comprising means for measuring the total eye aberration refraction comprises making the measurements under continuously varying lighting conditions from scotopic to photopic.

45. The instrument of claim 26 further comprising means for measuring the total eye aberration refraction comprises making the measurements at fixed intervals of light illumination to simulate scotopic, mesoptic and photopic conditions.

46. The instrument of claim 26 wherein the thin beams for the ray tracing to determine the total aberration refraction of the eye comprises a plurality of thin beams that impinge upon the corneal surface parallel to each other (far point light source); and a plurality of thin beams that impinge upon the corneal surface non-parallel to each other (near point light source).

* * * * *